(12) United States Patent
Xiao et al.

(10) Patent No.: US 9,181,578 B2
(45) Date of Patent: Nov. 10, 2015

(54) POLYNUCLEOTIDE MAPPING AND SEQUENCING

(75) Inventors: Ming Xiao, Huntington Valley, PA (US); Han Cao, Philadelphia, PA (US); Parikshit A. Deshpande, Princeton, NJ (US); Michael Boyce-Jacino, Princeton, NJ (US)

(73) Assignee: BIONANO GENOMICS, INC., San Diego, CA (US)

( * ) Notice: Subject to any disclaimer, the term of this patent is extended or adjusted under 35 U.S.C. 154(b) by 706 days.

(21) Appl. No.: 13/129,634

(22) PCT Filed: Nov. 18, 2009

(86) PCT No.: PCT/US2009/064996
§ 371 (c)(1),
(2), (4) Date: Jun. 23, 2011

(87) PCT Pub. No.: WO2010/059731
PCT Pub. Date: May 27, 2010

(65) Prior Publication Data
US 2011/0306504 A1    Dec. 15, 2011

Related U.S. Application Data

(60) Provisional application No. 61/115,704, filed on Nov. 18, 2008.

(51) Int. Cl.
*C12Q 1/68* (2006.01)

(52) U.S. Cl.
CPC ............... *C12Q 1/68* (2013.01); *C12Q 1/6806* (2013.01); *C12Q 1/6869* (2013.01)

(58) Field of Classification Search
CPC ........ C07H 21/02; C12Q 1/68; C12Q 1/6806; C12Q 1/6869
See application file for complete search history.

(56) References Cited

U.S. PATENT DOCUMENTS

| | | |
|---|---|---|
| 5,079,169 A | 1/1992 | Chu et al. |
| 5,314,829 A | 5/1994 | Coles |
| 5,356,776 A | 10/1994 | Kambara et al. |
| 5,427,663 A | 6/1995 | Austin et al. |
| 5,837,115 A | 11/1998 | Austin et al. |
| 5,867,266 A | 2/1999 | Craighead |
| 6,117,634 A | 9/2000 | Langmore |
| 6,197,557 B1 | 3/2001 | Makarov et al. |
| 6,210,896 B1 | 4/2001 | Chan |
| 6,214,246 B1 | 4/2001 | Craighead |
| 6,263,286 B1 | 7/2001 | Gilmanshin et al. |
| 6,344,319 B1 | 2/2002 | Bensimon et al. |
| 6,355,420 B1 | 3/2002 | Chan |
| 6,403,311 B1 | 6/2002 | Chan |
| 6,438,279 B1 | 8/2002 | Craighead et al. |
| 6,464,842 B1 | 10/2002 | Golovchenko et al. |
| 6,627,067 B1 | 9/2003 | Branton et al. |
| 6,635,163 B1 | 10/2003 | Han et al. |
| 6,696,022 B1 | 2/2004 | Chan |
| 6,753,200 B2 | 6/2004 | Craighead et al. |
| 6,762,059 B2 | 7/2004 | Chan et al. |
| 6,772,070 B2 | 8/2004 | Gilmanshin et al. |
| 6,790,671 B1 | 9/2004 | Austin |
| 6,927,065 B2 | 8/2005 | Chan et al. |
| 7,217,562 B2 | 5/2007 | Cao et al. |
| 7,262,859 B2 | 8/2007 | Larson et al. |
| 7,282,330 B2 | 10/2007 | Zhao et al. |
| 7,312,033 B2 | 12/2007 | Accola et al. |
| 7,316,769 B2 | 1/2008 | Craighead et al. |
| 7,351,538 B2 | 4/2008 | Fuchs et al. |
| 7,371,520 B2 | 5/2008 | Zhao et al. |
| 7,402,422 B2 | 7/2008 | Fuchs et al. |
| 7,427,343 B2 | 9/2008 | Han et al. |
| 7,670,770 B2 | 3/2010 | Chou et al. |
| 7,771,944 B2 | 8/2010 | Xiao et al. |
| 7,833,398 B2 | 11/2010 | Craighead et al. |
| 7,918,979 B2 | 4/2011 | Han et al. |
| 7,960,105 B2 | 6/2011 | Schwartz et al. |
| 8,168,380 B2 | 5/2012 | Chan et al. |
| 2001/0055764 A1 | 12/2001 | Empedocles et al. |
| 2002/0110818 A1 | 8/2002 | Chan |
| 2002/0119455 A1 | 8/2002 | Chan |

(Continued)

FOREIGN PATENT DOCUMENTS

| | | |
|---|---|---|
| CN | 1379857 A | 11/2002 |
| EP | 0 497 272 A1 | 8/1992 |

(Continued)

OTHER PUBLICATIONS

Xiao et al. Rapid DNA mapping by fluorescent single molecule detection. Nucleic Acids Res. 2007;35(3):e16. Epub Dec. 14, 2006.*
Chinese Office Action for Chinese Patent Application No. 200980154567.1 mailed on Mar. 13, 2013.
Chinese Office Action for Chinese Patent Application No. 200980154567.1 mailed on Nov. 21, 2013.
European Office Action for European Patent Application No. 09760398.9 mailed on Aug. 14, 2012.
International Search Report for International Application No. PCT/US2009/064996 mailed on Aug. 16, 2010.
Jo Kyubong et al., "A single-molecule barcoding system using nanoslits for DNA analysis", Proceedings of The National Academy of Sciences of The United States of America, Feb. 20, 2007, vol. 104, No. 8, pp. 2673-2678.
Vaandrager J W et al., "DNA fiber fluorescence in situ hybridization analysis of immunoglobulin class switching in B-cell neoplasia: aberrant CH gene rearrangements in follicle center-cell lymphoma", Blood, Oct. 15, 1998, vol. 92, No. 8, pp. 2871-2878

(Continued)

*Primary Examiner* — Michele K Joike
(74) *Attorney, Agent, or Firm* — Knobbe Martens Olson & Bear LLP

(57) ABSTRACT

The present invention provides methods of obtaining structural information about a biopolymer sample. The methods include labeling portions of a biopolymer, such as DNA or RNA, linearizing the biopolymer in some cases, and determining the distance between the labels. The user can then compare different samples' between-label distances to qualitatively compare different samples and to assay a given sample for additions or deletions of nucleotides in the regions flanked by the labels. The methods also permit sequencing of biopolymers.

17 Claims, 20 Drawing Sheets

(56) References Cited

U.S. PATENT DOCUMENTS

| | | | |
|---|---|---|---|
| 2002/0123063 | A1 | 9/2002 | Gjerde et al. |
| 2002/0197639 | A1 | 12/2002 | Shia et al. |
| 2003/0066749 | A1 | 4/2003 | Golovchenko et al. |
| 2003/0104428 | A1 | 6/2003 | Branton et al. |
| 2003/0209314 | A1 | 11/2003 | Guo et al. |
| 2003/0219792 | A1 | 11/2003 | Armes et al. |
| 2003/0219805 | A1 | 11/2003 | Kelman et al. |
| 2003/0232346 | A1* | 12/2003 | Su .................................. 435/6 |
| 2003/0235854 | A1 | 12/2003 | Chan et al. |
| 2004/0009612 | A1 | 1/2004 | Zhao et al. |
| 2004/0033515 | A1 | 2/2004 | Cao et al. |
| 2004/0166025 | A1 | 8/2004 | Chan |
| 2004/0195098 | A1 | 10/2004 | Broadley et al. |
| 2004/0197843 | A1 | 10/2004 | Chou et al. |
| 2005/0082204 | A1 | 4/2005 | Schwartz et al. |
| 2005/0208538 | A1 | 9/2005 | Kurn et al. |
| 2005/0250117 | A1 | 11/2005 | Su et al. |
| 2006/0011862 | A1 | 1/2006 | Bernstein |
| 2006/0068440 | A1 | 3/2006 | Chan et al. |
| 2006/0199202 | A1 | 9/2006 | Lyamichev et al. |
| 2006/0275911 | A1 | 12/2006 | Wang et al. |
| 2007/0128083 | A1 | 6/2007 | Yantz |
| 2007/0161028 | A1 | 7/2007 | Schwartz et al. |
| 2007/0219367 | A1 | 9/2007 | Shchepinov et al. |
| 2008/0003689 | A1 | 1/2008 | Lee |
| 2008/0085552 | A1 | 4/2008 | Larson et al. |
| 2008/0103296 | A1 | 5/2008 | Zhao |
| 2008/0242556 | A1 | 10/2008 | Cao et al. |
| 2008/0254549 | A1 | 10/2008 | Fuchs |
| 2011/0171634 | A1 | 7/2011 | Xiao et al. |
| 2011/0171741 | A1 | 7/2011 | Wang et al. |
| 2011/0210272 | A1 | 9/2011 | Chan et al. |
| 2011/0306504 | A1 | 12/2011 | Xiao et al. |
| 2012/0196382 | A1 | 8/2012 | Chan et al. |
| 2012/0217161 | A1 | 8/2012 | Chan et al. |

FOREIGN PATENT DOCUMENTS

| | | |
|---|---|---|
| JP | 2003-507026 | 2/2003 |
| JP | 2005-505754 | 2/2005 |
| JP | 2005-518215 | 6/2005 |
| JP | 2005-524413 | 8/2005 |
| JP | 2005-533636 | 11/2005 |
| WO | WO 98/39485 | 9/1997 |
| WO | WO 98/35012 A | 8/1998 |
| WO | WO 00/079257 | 12/2000 |
| WO | WO 01/13088 A1 | 2/2001 |
| WO | WO 02/065138 | 8/2002 |
| WO | WO02/099398 | 12/2002 |
| WO | WO 03/010289 A2 | 2/2003 |
| WO | WO 03/072805 A2 | 9/2003 |
| WO | WO 03/106620 A2 | 12/2003 |
| WO | WO 03/106693 | 12/2003 |
| WO | WO2005078137 | 8/2005 |
| WO | WO 2006/102321 | 9/2006 |
| WO | WO 2007/065025 | 6/2007 |
| WO | WO 2010/002883 | 6/2009 |
| WO | WO 2010/002883 | 1/2010 |
| WO | WO 2010/053980 A2 | 5/2010 |
| WO | WO 2010/059731 A2 | 5/2010 |
| WO | WO 2011/050147 | 4/2011 |

OTHER PUBLICATIONS

Amann R et al., "In situ visualization of high genetic diversity in a natural microbial community", Journal of Bacteriology, American Society for Microbiology, Washington, DC; US, vol. 178, No. 12, Jun. 1, 1996, pp. 3496-3500.

Reil Heide et al., "Clinical validation of a new triplex real-time polymerase chain reaction assay for the detection and discrimination of Herpes simplex virus types 1 and 2", The Journal of Molecular Diagnostics: Jul. 2008, vol. 10, No. 4, pp. 361-367.

Das et al., "Single molecule linear analysis of DNA in nano-channel labeled with sequence specific fluorescent probes", Nucleic Acids Research, 2010, vol. 38, No. 18, 8 pages.

Notice of Allowance dated Sep. 18, 2013 in U.S. Appl. No. 13/001,697.

Cai et al., "High-resolution restriction maps of bacterial artificial chromosomes constructed by optical mapping." Proc. Natl. Acad. Sci. USA, vol. 95, No. 7, pp. 3390-3395 (1998).

Cao et al., "Fabrication of 10nm enclosed nanofluidic channels." Appl. Phys. Lett., 81:174-176 (2002).

Cao et al., "Gradient nanostructures for interfacing microfluidics and nanofluidics." Appl. Phys. Lett., 81:3058-3060 (2002).

Castro et al., "Single-molecule detection of specific nucleic acid sequences in unamplified genomic DNA." Analytical Chemistry, 69(19):3915-3920 (1997).

Olivier et al., "High-throughput genotyping of single nucleotide polymorphisms using new biplex invader technology." Nucleic Acids Research, vol. 30, No. 12, p. E53 (2002).

Piepenburg et al., "DNA detection using recombination proteins." PLOS Biology, vol. 4, No. 7, e204 (2006).

Reccius et al., "Compression and free expansion of single DNA molecules in nanochannels." Physical Review Letters, 95:268101-1 (2005).

Tegenfeldt et al., "From the Cover: The dynamics of genomic-length DNA molecules in 100-nm channels." Proc. Natl. Acad. Sci. USA, 101(30):10979-83 (2004).

International Search Report dated Apr. 7, 2011 for PCT Application No. PCT/US2010/053513 filed Oct. 21, 2010.

Written Opinion of International Search Authority dated Apr. 21, 2011 for PCT Application No. PCT/US2010/053513 filed Oct. 21, 2010.

International Search Report and Written Opinion of International Search Authority dated Oct. 9, 2010 for PCT Application No. PCT/US2009/049244 filed Jun. 30, 2009.

Kuhn et al., "Labeling of unique sequences in double-stranded DNA at sites of vicinal nicks generated by nicking endonucleases." Nucleic Acids Research, 36(7):e40:1-10 (2008).

Chan et al., "DNA mapping using microfluidic stretching and single-molecule detection of fluorescent site-specific tags." Genome Research, 14(6):1137-1146 (2004).

Phillips et al., "Application of single molecule technology to rapidly map long DNA and study the conformation of stretched DNA." Nucleic Acids Research, 33(18):5829-5837 (2005).

Written Opinion and Search Report of Intellectual Property Office of Singapore dated Jan. 9, 2013 for Singapore Patent Application No. 201009665-0 filed Jun. 30, 2009.

Fu D-J et al., "Sequencing Double-Stranded DNA by Strand Displacement", Nucleic Acids Research, Information Retrieval Ltd., vol. 25, No. 3, (Jan. 1997), pp. 677-679.

Extended European Search Report for European patent application No. 13179160.0 mailed on Oct. 22, 2013.

Office Action for European patent application No. 09774334.8 mailed on Oct. 18, 2013.

Office Action dated May 13, 2014 issued in Japanese Patent Application No. 2011-537585 filed Nov. 18, 2009.

Austin et al.: "Scanning the Controls: Genomics and Nanotechnogloy," IEEE Transactions on Nanotechnology 1: 12-18, 2002.

Cai et al.: "Ordered restriction endonuclease maps of artificial chromosomes created by optical mapping on surfaces," PNAS 92: 5164-8, 1995.

Chan et al.: "DNA mapping using microfluidic stretching and single molecule detection of fluorescent site-specific tags," Genome Research 14: 1137-1146, 2004.

Chang et al.: "DNA-Mediated Fluctuations in Ionic Current through Silicon Oxide Nanopore Channels," Nano Letters 4: 1551-1556, 2004.

Chen et al.: "Atomic Layer Deposition to Fine-Tune the surface Properties and Diameters of Fabricated Nanopores," Nano Letters 4: 1333-1337, 2004.

Chen et al.: "Probing Single DNA Molecule Transport Using Fabricated Nanopores," Nano Letters 4: 2293-2298, 2004.

Chinese Office Action dated Jun. 29, 2012 for Chinese Patent Application No. 200880017550.7.

Chinese Office Action dated Nov. 14, 2012 for Chinese Patent Application No. 200880017550.7.

(56) References Cited

OTHER PUBLICATIONS

Chou et al.: "A Microfabricated Device for Sizing and Sorting DNA Molecules," Proc. Natl. Acad. Sci. USA, Jan. 1999, 96, 11-13.
Conrad et al.: "A high-resolution survey of deletion polymorphism in the human genome," Nature Genetics 38: 75-81, 2006.
Czaplewski et al.: "Nanofluidic channels with elliptical cross sections formed using a nonlithographic process," Applied Physics Letters, Dec. 8, 2003, 83(23), 836-4838.
Deamer et al.: "Characterization of Nucleic Acids by Nanopore Analysis," Acc Chem Res 35: 817-825, 2002.
Deegan et al.: "Contact line deposits in an evaporating drop," Physical Review E, Jul. 2000, 62(1), 756-765.
Dietrich et al.: "Advances in the Development of a Novel Method to be used in Proteomics using Gold Nanobeads," U/trasens/tive and Single-Molecule etection Technologies, edited by Jorg Enderlein, et al, Proc. of SPIE vol. 6092, 6092C (2006).
Eichler: "Widening the spectrum of human genetic variation," Nature Genetics 38: 9-11, 2006.
European Extended Search Report dated Jun. 18, 2014 for European Patent Application No. 13150068.8.
European Partial Search Report dated Feb. 5, 2014 for European Application No. EP 13150068.8.
European Search Report dated May 31, 2013 for European Application No. EP 12194842.6.
Examination Report dated Dec. 23, 2010 for European Application No. 08744609.2.
Examination Report dated Jul. 23, 2012 for European Application No. 08744609.2.
Examination Report dated Nov. 9, 2012 in Australian Application No. 2008232616.
FDA Redbook 2000 Genotoxicity Tests, available at www.cfsan.fda.gov.
Final Decision of Rejection dated Aug. 13, 2013 for Japanese Application 2010-501259.
Gad et al.: "Bar code screening on combed DNA for large rearragements of the BRCA1 and BRCA2 genes in French breast cancerfamilies." J Med Genet 39: 17-21, 2002.
Gad et al.: "Color bar coding the BRCA1 gene on combed DNA: A useful strategy for detecting large gene arrangements." Genes, Chromosomes and Cancer 31: 5-84, 2001.
Gracheva et al.: "Simulation of the electric response of DNA translocation through a semiconductor nanopore-capacitor," Nanotechnology 17: 622-633, 2006.
Guidance for industry S2B Genotoxicity: A standard Battery for Genotoxicity Testing of Pharmaceuticals, Jul. 1997, ICH.
Guo et al: "Fabrication of Size-Controllable Nanofluidic Channels by Nanoimprinting and its Application for DNA Stretching", 2004, 4, 69-73.
Hashioka et al.: "Simple and Quick Detection of Target DNA by Hybridization in Nano Gap Channel Array." 9th International Conference on Miniaturized Systems or Chemistry and Life Sciences, vol. 1, pp. 730-732 (2005).
Henriquez et al.: "The resurgence of Coulter counting for analyzing nanoscale objects," The Analyst, 2004, 129, 478-482.
Hinds et al.: "Common deletions and SNPs are in linkage disequilibrium in the human genome," Nature Genetics 38: 82-85, 2006.
Howorka et al.: "Kinetics of duplex formation for individual DNA strands within a single protein nanopore," PNAS 98: 12996-13001, 2001.
Howorka et al.: "Sequence-specific detection of individual DNA strands using engineered nanopores," Nature Biotechnology 19: 636-639, 2001.
International Preliminary Report on Patentability dated Feb. 23, 2009 for PCT Application No. PCT/US2007/016408.
International Search Report and Written Opinion dated Jan. 19, 2009 for PCT Application No. PCT/US2008/058671.
International Search Report dated Aug. 17, 2012 for Application PCT/US2011/057115.

Japanese Office Action dated Jul. 24, 2012 for Japanese Patent Application No. 2009-520847 (English translation thereof is enclosed).
Johansson et al.: "Primary vs. secondary neoplasia-associated chromosomal abnormalities-balanced rearrangements vs genomic imbalances?" Genes, Chromosomes and Cancer 16: 155-163, 1996.
Kasianowicz et al.: "Characterization of individual polynucleotide molecules using a membrane channe l," PNAS 93: 13770-13773, 1996.
Koppal et al.: "Spanning the Drug Pipeline," Drug Discovery & Development, Sep. 13, 2005, 1 page, http://www.dddmag.com.
Li et al.: "Ion-beam sculpting at nanometer length scales," Nature 412: 166-169, 2001.
Li et al.: "DNA molecules and configurations in a solid-state nanopore microscope," Nature Materials 2: 611-615, 2003.
Li, et al.: "Sacrificial polymers for nanoflui d channels in biological applications," Nanotechnology, 2003, 14, 578-583.
Mannion et al., Conformational Analysis of Single DNA Molecule Undergoing Entropically Induced Motion in Nanochannels, Biophysical Journal, Jun. 2006, vol. 90, pp. 4538-4545.
McCarroll et al.: "Common deletion polymorphisms in the human genome," Nature Genetics 38: 86-92, 2006.
McGee et al.: "New In Vitro, Modeling Tools May Cut Tox Attrition," Drug Discovery & Development, Aug. 4, 2005, 4 pages, http://wvvw.dddmag.com.
McGee, et al.: "Small-Animal Models Advance in Vivo ADME-Tox", Drug Discovery & Development, Jul. 5, 2005, 3 pages, http://wvvw.dddmag.com.
Meller et al.: "Rapid nanopore discrimination between single polynucleotide molecules," PNAS 97: 1079-1084, 2001.
Meller et al.: "Voltage-Driven DNA Translocations through a Nanopore," Physical Review Letters 86: 3435-3438, 2001.
Meng et al.: "Optical mapping of lambda bacteriophage clones using restriction endonucleases," Nat Genet 9: 432-438, 1995.
Mijatovic et al., "Technologies for nanoflui di csystems: top-down vs. bottom-up—a review," Lab on a Chip, Royal Society of Chemistry, Cambridge, GB, Jan. 2005, vol. 5, 492-500.
Molecular Devices website, product page for Axopatch 200B: No date present NB/ http://wvvw.moleculardevices.com/pages/instruments/cn__axopatch200b.html, submitted 2015.
Nagata et al.: "Degradation of chromosomal DNA during apoptosis," Cell Death and Differentiation 10: 108-116, 2003.
Nath et al.: "A System for Micro/Nano Fluidic Flow", Diagnostics, 2005, Biomedical Microdevices, 7, 169-177.
Notice of Allowance dated Dec. 11, 2013 for Canadian Patent Application No. 2658122.
Notice of Allowance dated Jan. 23, 2014 for Australian Patent Application No. 2007338862.
Office Action dated Aug. 12, 2014 issued in Korean Patent Application No. 10-2009-7022447.
Office Action dated Dec. 9, 2013 for Japanese Patent Application No. 2009-520847.
Office Action dated Feb. 10, 2015 for Australian Patent Application No. AU2009267086.
Office Action dated Feb. 5, 2013 for Japanese Patent Application No. 2009-520847.
Office Action dated Jan. 4, 2012 for Chinese Patent Application No. 200780034694.9.
Office Action dated Jan. 7, 2015 for Australian Patent Application No. 2011316989.
Office Action dated Mar. 28, 2013 for Canadian Patent Application No. 2658122.
Office Action dated May 9, 2012 for Australian Patent Application No. 2007338862.
Office Action dated May 9, 2012 of U.S. Appl. No. 13/001,697.
Office Action dated Nov. 5, 2012 for Chinese Patent Application No. 200780034694.9.
Office Action dated Sep. 25, 2012 for Japanese Application 2010-501259.
Office Action dated Sep. 29, 2014 for Canadian Patent Application No. 2682275.
Office Action dated Jan. 20, 2015 for Japanese Patent Application No. 2013-258107.

(56) References Cited

OTHER PUBLICATIONS

Office Action dated Jan. 30, 2015 for Korean patent application No. 10-2011-7000192.
Purves et al.: "Genotoxicity testing: Current Practices and Strategies Used by the Pharmaceutical Industry," Mutagenesis, 1995, vol. 10 No. 4 pp. 297-312.
Reccius et al.: "Compression and Free Expansion of Single DNA Molecules in Nanochannels," Phys. Rev. Letts., Dec. 21, 2005, 95, 268101-1-268101-4.
Turner, et al.: "Monolithic nanofluid sieving structures for DNA manipulation", Journal of Vacuum Science and Technology, 16, 3835, 1998.
Slater, et al., "Bidirectional Transport of Polyelectrolytes Using Self-Modulating Entropic Ratchets," Physical Review Letters, The American Physical Society, 78(6), Feb. 1997, 1170-1173.
Storm et al.: "Fabrication of solid-state nanopores with single-nanometer precision," Nature Materials 2: 537-540, 2003.
Storm et al.: "Fast DNA Translocation through a Solid-State Nanopore," Nano Letters 5: 1193-1197, 2005.
Technology Research News, LLC, "Melted fibers make nano channels," Jan. 14, 2004, Retrieved from the internet at URL <http://wvvw.trnmag.com/Stories/2004/011404/Me | ted_fibers_make_nano_channe | s_Brief.
Tegenfeldt et al.: "Micro and nanofluidics for DNA analysis," Anal Bioanal Chem 378: 1678-1692, 2004.
Tegenfeldt et al.: "The dynamics ofgenomic-length DNA molecules in 100-nm channe | s," PNAS 101: 10979-10983, 2004b.
Volkmuth et al.: "DNA electrophoresis in microlithographic arrays", Department of Physics, Princeton University, Nature, vol. 358, Aug. 13, 1992, pp. 600-602.
Wade et al.: "The Quest for the $1,000 Human Genome" The New York Times, Jul. 18, 2006.
Wong et al.: "Deformation of DNA molecules by hydrodynamic focusing," J Fluid Mechanics 497: 55-65, 2003.
W. Volkmuth et al., Observation of Electrophoresis of Single DNA Molecules in Nanofabricated Arrays, American Society for Biochemistry and Molecular Biology Biophysical Society Joint Meeting, Houston Texas, Feb. 9-13, 1992, Abstracts, FASEB Journal, vol. 6, No. 1, Jan. 1, 1992. 3 pages.
Office Action in U.S. Appl. No. 13/710,180, mailed Mar. 14, 2014.
Office Action in U.S. Appl. No. 13/880,365, mailed Dec. 8, 2014.
Japanese Office Action for Japanese Patent Application No. 2011-516813 dated Jan. 14, 2014 by Japanese Patent Office.
Japanese Office Action for Japanese Patent Application No. 2011-516813 mailed Oct. 14, 2014 by Japanese Patent Office.
Chinese Office Action for Chinese Patent Application No. 201180060380.2 dated Feb. 24, 2014 by Chinese Patent Office.
European Office Action for European Patent Application No. 09774334.8 mailed Aug. 28, 2014 by European Patent Office.
Australian Office Action for Australian Patent Application No. 2011316989 mailed Jan. 7, 2015 by Australian Patent Office.

\* cited by examiner

| Exon-1 | Exon1 133bp | Exon2 87bp | Exon3 87bp | Exon4 66bp | Exon5 56bp | Exon7 127bp | Exon9 266bp | Exon10 93bp | Exon11 87bp | Exon12 113bp | Exon13 216bp | Exon14 87bp |
|---|---|---|---|---|---|---|---|---|---|---|---|---|

*FIG. 2B*

D   Four color eight probes can barcode 65536 genes for gene expression and splicing pattern

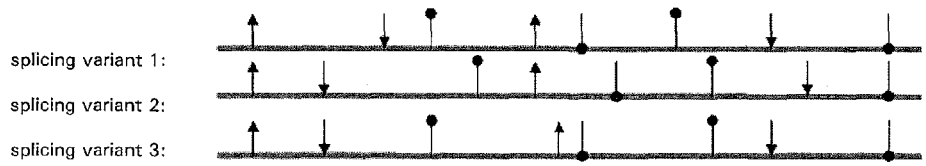

splicing variant 1:
splicing variant 2:
splicing variant 3:

Gene 2 with Green-blue-yellow-red-green-blue-yellow-red barcode,
the different distances between color define each splicing variant within the gene:

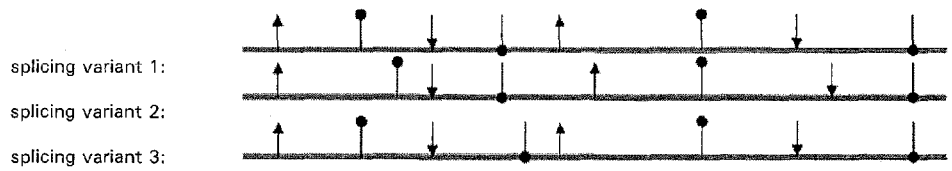

splicing variant 1:
splicing variant 2:
splicing variant 3:

Gene 3

↑ = green     ↑ = blue

↓ = yellow    ↓ = red

*FIG. 2D*

First step: hybridization of a 5mer probe. *On average*, 5mer will hybridize 1024 bp apart along the template.

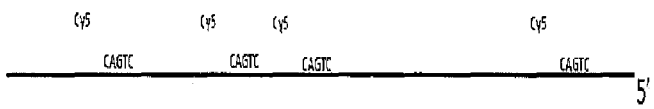

Second step: polymerase will incorporate 4 labeled terminators, A,C,G,T, specificity is very high due to a. hybridization, b. polymerase can incorporate next base only if perfect match occurs.

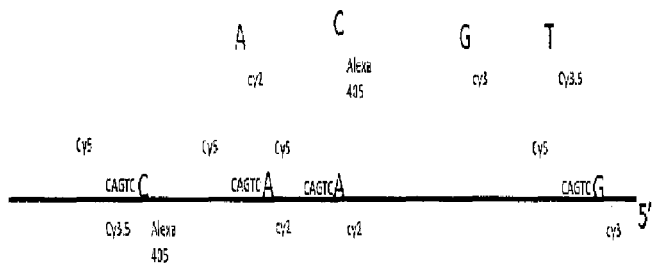

Third step imaging: multicolor STORM to localize all four events in space.
Now we barcode all four incorporation events described in above figure,
and we read 4 bases sequentially at four different loci. Total 4x6=24bp are read after first cycle.
More importantly, the hybridization location was precisely localized with super-resolution imaging, which will guide next cycle base reading.

*FIG. 4*

In the next cycle, we can choose 4 more 5mer probes based on the previous cycle to hybridize the same template. They will hybridize on the same loci as the previous cycle, which we detected and recorded the locations through the super resolution imaging.

CAGTCC    CAGTCA    CAGTCG    CAGTCT

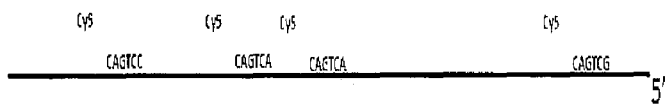

Repeat the incorporation step of 4 labeled terminators, A,C,G,T.

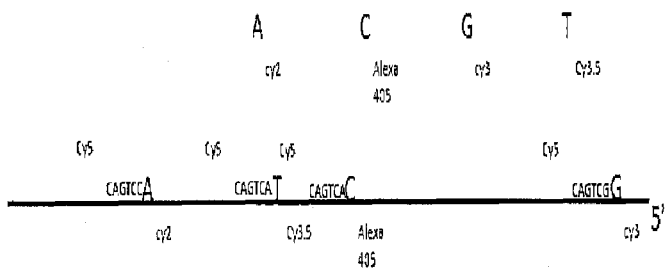

After two cycles, we read 7x4=28 bases. This can be easily extended to 5-10 cycles, which Total 4x10=40 bases.

FIG. 5

To add complexity and throughput, we can perform multiplex hybridization with different color probes. In the example below, we start with four different color hybridization probes.

Assuming 12 hybridization events, after incorporation, we read 12 bases, and in total, 12x5=60bp will be read.

In this scenario, one needs to balance the probes chosen for hybridization and sequential polymerase incorporation to maximize power of multiplicity.

FIG. 6

POLYNUCLEOTIDE MAPPING AND SEQUENCING

RELATED APPLICATIONS

Cross-Reference to Related Applications

This application is the National Stage of International Application No. PCT/US2009/064996, filed Nov. 18, 2009, which claims the benefit of U.S. Provisional Application No. 61/115,704, filed Nov. 18, 2008, the disclosures of which are incorporated herein by reference in their entireties for any and all purposes.

TECHNICAL FIELD

The disclosed invention relates to the field of nucleic acid sequencing and to the field of molecular imaging. The disclosed invention also relates to the field of nanotechnology.

BACKGROUND

With advances in molecular biology techniques has come increased interest in analyzing smaller and smaller samples with ever-increasing resolution and precision. Some of this is driven by the realization that population heterogeneity can often obscure salient features of a sample. Limited sample volume is also a consideration for some applications.

While existing techniques are, in theory, capable of extracting significant information from physically small samples, the effectiveness of such techniques has been limited by their ability to resolve structural features on such small samples. Accordingly, there is a need in the art for methods and related devices capable of obtaining genomic information based on single molecules or other physically small samples. The value of such methods would be enhanced if such methods were capable of improving upon the 1000 bp (1 kb) accuracy achieved by current techniques.

SUMMARY

In meeting the described challenges, the claimed invention first provides methods for assaying for the presence or relative positions of one or more exons, the methods comprising labeling first and second locations on a biopolymer with, respectively, a first and a second label such that the first and second labels flank a first region of the biopolymer that includes at least one constant exon; and linearizing the biopolymer and correlating the distance between the first and second labels to the presence, absence, or relative position of an alternative exon in said first region of the biopolymer.

In a second aspect, the present invention provides methods of obtaining structural information about a DNA sample, comprising nicking a first double-stranded DNA sample with a sequence-specific nicking endonucleoase; incorporating one or more dye-labeled nucleotides at two or more nicking sites effected by the nicking endonuclease; linearizing a portion of the first double-stranded DNA sample that includes at least two dye-labeled nucleotides; and registering the relative positions of two or more labeled dye-labeled nucleotides.

Also provided are methods of obtaining sequence information about a nucleic acid biopolymer, comprising binding a first fluorescently labeled sequence specific probe having a first binding sequence to a single-stranded nucleic acid biopolymer; contacting the single-stranded nucleic acid biopolymer with a first terminator nucleotide bearing a first fluorescent label, with a second terminator nucleotide bearing a second fluorescent label, with a third terminator nucleotide bearing a third fluorescent label, and with a fourth terminator nucleotide bearing a fourth fluorescent label; and linearizing and illuminating the nucleic acid biopolymer so as to determine the presence or relative positions of the first terminator nucleotide, the second terminator nucleotide, the third terminator nucleotide, the fourth terminator nucleotide, or any combination thereof, adjacent to the first labeled sequence-specific probe.

The invention also provides methods of obtaining structural information about a nucleic acid biopolymer, comprising contacting a double-stranded biopolymer with a nicking endonuclease so as to effect a first nicking site; contacting the first nicking site with a first terminator nucleotide bearing a fluorescent label A, with a second terminator nucleotide bearing a fluorescent label B, with a third terminator nucleotide bearing a fluorescent label C, and with a fourth terminator nucleotide bearing a fluorescent label D; and linearizing and illuminating the double-stranded biopolymer so as to determine the relative positions of the first terminator nucleotide, the second terminator nucleotide, the third terminator nucleotide, the fourth terminator nucleotide, or any combination thereof.

Further provided are kits for performing multiplex hybridization, comprising a plurality of hybridization probes each of a different color; and instructions for applying at least two of the plurality of hybridization probes to a nucleic acid sample and linearizing and imaging at least one of the hybridized nucleic acids.

BRIEF DESCRIPTION OF THE DRAWINGS

The summary, as well as the following detailed description, is further understood when read in conjunction with the appended drawings. For the purpose of illustrating the invention, there are shown in the drawings exemplary embodiments of the invention; however, the invention is not limited to the specific methods, compositions, and devices disclosed. In addition, the drawings are not necessarily drawn to scale. In the drawings:

FIG. 2B lists the size of each exon (alternative exons shown as shaded) of each exon present in the MAPT gene;

FIG. 2D illustrates a multiplexed barcoding scheme;

FIG. 4 depicts the first cycle of a sequencing reaction;

FIG. 5 depicts the second sequencing cycle begun in FIG. 4;

FIG. 6 demonstrates that a multiplexed sequencing scheme dramatically increases throughput;

Cy3 dye molecules 30 nm and 60 nm apart, which was in good agreement with the 94 bp and 172 bp distances between the three (3) Cy3 probes.

FIG, 8A depicts a model system of a 741 bp PCR product used to demonstrate the resolution of SHRIMP and SHREC;

FIG, 8B illustrates the imaging results after labeled DNA molecules were linearized on glass surface—the distances between Cy3-Cy5 pairs was 37±5 nm (32 nm expected) and 91±5 nm (87 nm expected), and the distance between Cy3-Cy3 pair to be 56±3 nm (58 nm expected) (FIG, 4), demonstrating excellent agreement;

FIG, 9 depicts a sample, nonlimiting embodiment of the claimed methods of ascertaining structural information regarding genetic material;

FIG, 10 depicts a second sample, non-limiting embodiment of the claimed methods of ascertaining structural information regarding genetic material;

FIG, 11 depicts a non-limiting embodiment of the claimed methods; and

FIG, 12 depicts a further, non-limiting embodiment of the claimed methods.

Figure 13:
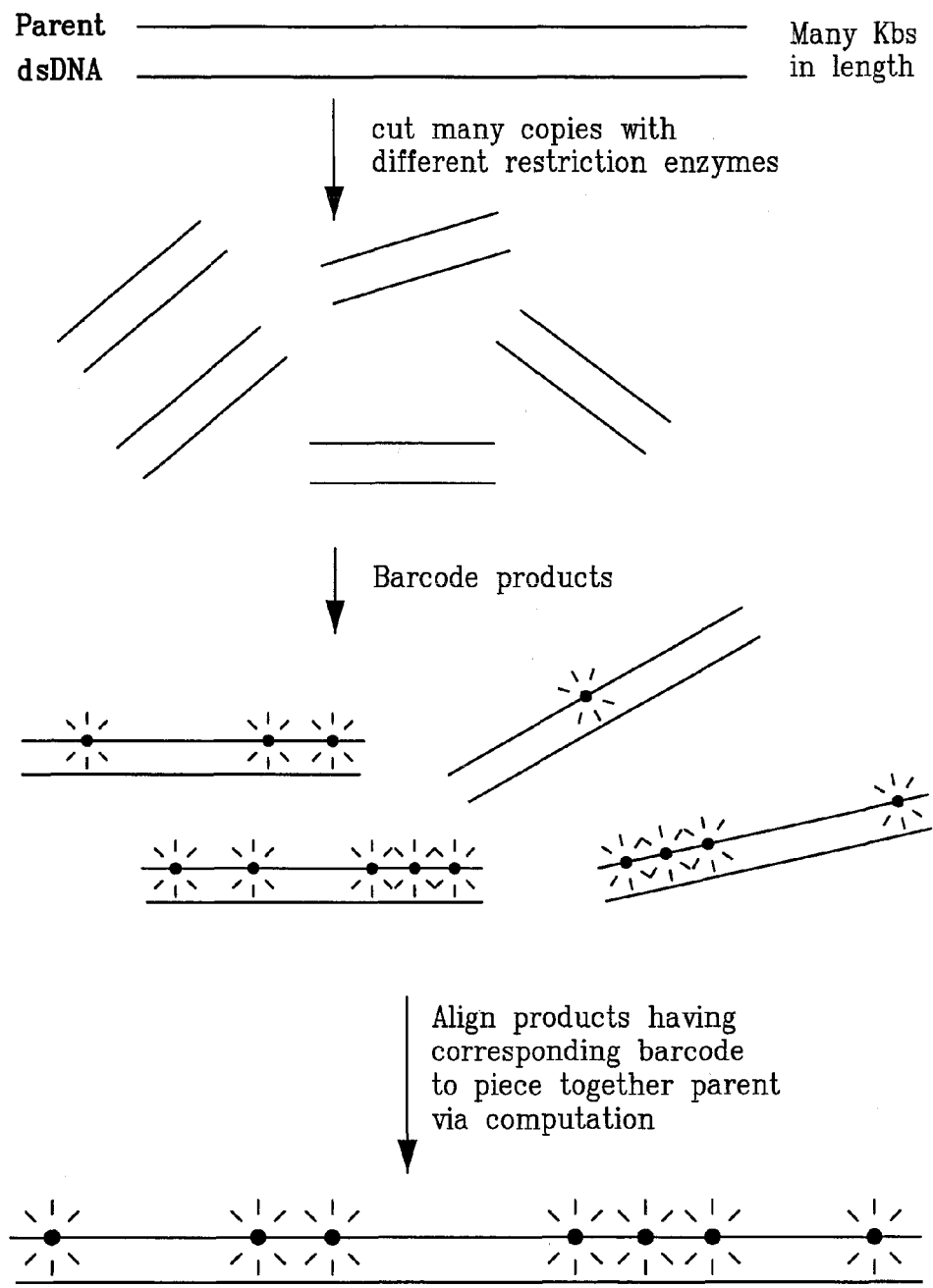

FIG. 13 depicts the steps of digesting a parent sample of DNA, placing barcodes on the products that result from the digestion, and the alignment of products having corresponding barcodes so as to piece together the parent and the effective barcode for the parent.

DETAILED DESCRIPTION OF ILLUSTRATIVE EMBODIMENTS

The present invention may be understood more readily by reference to the following detailed description taken in connection with the accompanying figures and examples, which form a part of this disclosure. It is to be understood that this invention is not limited to the specific devices, methods, applications, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

It is to be appreciated that certain features of the invention which are, for clarity, described herein in the context of separate embodiments, may also be provided in combination in a single embodiment. Conversely, various features of the invention that are, for brevity, described in the context of a single embodiment, may also be provided separately or in any subcombination. Further, reference to values stated in ranges include each and every value within that range.

In a first embodiment, the present invention provides methods of assaying for the presence or even relative positions of one or more exons. These methods suitably include labeling first and second locations on a biopolymer sample with, respectively, a first and a second label such that the first and second labels flank a first region of the biopolymer sample that includes at least one constant exon. The user then correlates the distance between the first and second labels to the presence or absence (or relative position) of an alternative exon (i.e., an exon that does not appear in every mRNA) in said first region of the biopolymer. (The biopolymer is suitably DNA that is complementary to an mRNA; such DNA is easily synthesized by those of ordinary skill in the art.)

In some embodiments, the first and second labels are the same fluorophore. A wide range of fluorophores are suitable for the present inclwention, including the Cy—family of fluorophores. Other fluorophores will be known to those of skill in the art; a listing of fluorophores is found at, e.g., http://info.med.yale.edu/genetics/ward/tavi/FISHdyes2.html. The labels may be of the same fluorophore, but may also be of different fluororphores.

The user suitably correlates the distance between the first and second labels to the presence, absence, or both of one or more alternative exons (or even the exons' relative positions) comprises comparing the distance between the first and second labels present on the biopolymer sample to the distance between labels that flank the first region of the biopolymer known not to contain an alternative axon. This is suitably accomplished by linearizing that region of the biopolymer that includes the fluorescent labels. Linearizing of biopolymers is discussed in detail in U.S. patent application Ser. No. 10/484,293 (granted Nov. 9, 2009), the entirety of which is incorporated herein by reference for all purposes.

The correlating suitably includes comparing the distance between the first and second labels to the distance between the first and second locations on a biopolymer lacking an alternative exon between the first and second locations.

This is illustrated by, e.g., FIG, 2C, which figure depicts at "zero" a biopolymer having no alternative exons. Embodiment "2" in that figure depicts a biopolymer having alternative exon "2", which alternative exon may be detected by observing that the exon results in an increased separation distance (342 bp) between the Cy3 and Cy5 dyes that were only separated by 255 bp in the no-alternative-exon biopolymer shown at the top of the figure.

FIG, 2B is a table showing the size of each of the exons (alternative exons are shown by shaded blocks) present in the MAPT gene. FIG, 2A illustrates, generally, the various splicing permutations possible in the MAPT gene. As shown in that figure, exons 2, 3 and 10 are considered "alternative" exons, and may—or may not—be present in MAPT mRNA.

The user may also suitably label third, fourth, or even additional locations on the biopolymer with additional labels (with, e.g., labeled nucleotides). Such additional labels may include the same fluorophore as the first or second labels, or may include fluorophores distinct from those on the first and second labels. The user may then correlate the distance between the third label and the first label, the third label and the second label, or both, to the presence or absence of an alternative exon disposed between the third label and the first label, between the third label and the second label, or both. The correlation may also provide the relative positions of one or more labels.

This is also shown by FIG, 2. In embodiment labeled "2+10", the biopolymer includes alternative exons 2 and 10, which exons are disposed between the first and second and second and third labels (reading from left to right) on the biopolymer. The user can then determine the presence (or relative positions) of these exons by comparing the distances between the labels on the "2+10" embodiment against the distances between the labels on the "zero" embodiment shown at the top of the figure.

In addition to gleaning information about the structure of the biopolymer under study from the distance between the labels, the user can also obtain structural information based on the relative order of two or more probes, which is facilitated by the probes bearing differently-colored fluorophores. For example, if three probes (red, yellow, and green) are used, a sequence to which the probes bind in the order red-yellow-green is structurally different from a sequence to which the probes bind in the order yellow-red-green. Thus, the user may glean information about a sample by observing both the relative order in which probes are bound/arranged on the sample as well as the relative distances between probes.

Returning to the nonlimiting example described above, the user that compares two samples could determine—by accounting for the relative order of the probes and the distances between the probes—that two samples differ in (1) the order in which certain nucleotide sequences appeal (evidenced by probes being in different orders on the different samples) and (2) the number of, e.g., copy variations in a given sample (evidenced by certain probes being father apart on one sample than on another).

The labels are suitably separated from one another by about 30 bp to about 1000 bp, but more suitably about 30 bp. As described elsewhere here, a number of techniques (e.g., SHRIMP, FIONA, SHREC, or other techniques known to those of ordinary skill in the art) enable resolution of labels separated from one another by small distances on the order of only hundreds or even tens of base pairs.

In another aspect, the present invention provides methods of obtaining structural information about a DNA sample. These methods suitably include nicking a first double-stranded DNA sample with a sequence-specific nicking endonuclease. Such "nickases" are known the art, and are available from, e.g., New England Biolabs.

The methods suitably include incorporating one or more dye-labeled nucleotides at two or more nicking sites effected by the nicking endonuclease. Depending on the endonuclease and the sample under analysis, the nickage may effect one, two, or multiple nicking sites along the length of the sample. The labeled nucleotides are suitably incorporated into the biopolymer via a polymerase. The labeled nucleotides are, in suitable embodiments, terminator nucleotides that counteract the effect of the polymerase and do not promote further chain lengthening. The nucleotides may bear the same fluorophore label or different labels, depending on the needs of the user.

The methods also suitably include linearizing a portion of the first double-stranded DNA sample that includes at least two dye-labeled nucleotides. Once the labeled DNA is linearized, the user may then register or otherwise account for the positions of two or more labeled dye-labeled nucleotides for use in further analysis.

Figure 9:
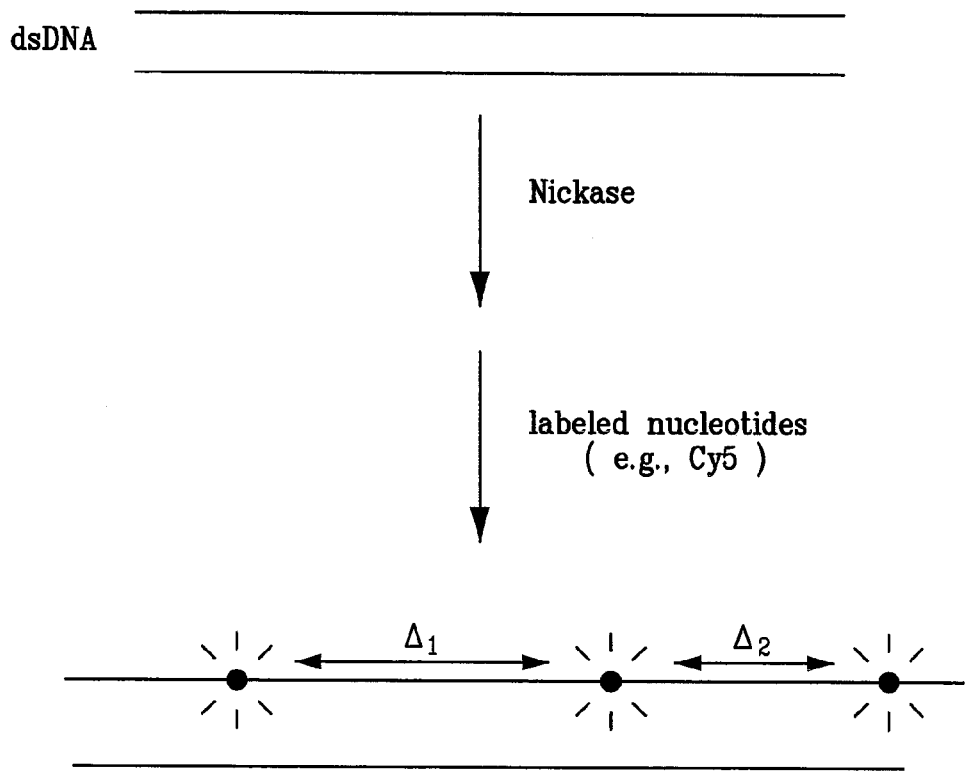

One such analysis includes correlating the relative positions of two or more dye-labeled nucleotides to one or more structural characteristics of the first double-stranded DNA sample. This may entail—as shown in FIG. 9—determining the distance between two labels that are known to flank a region of interest, such as a region known to contain a certain mutation or copy number variation in some individuals. By comparing the between-labels distance on the sample to the between-labels distance on a control sample (or the between-labels distance on another sample taken from another individual or individuals), the user can determine whether the subject under analysis may have (or not have) a particular mutation.

In some embodiments, the "barcode" derived from the relative positions of the labels present on the biopolymer sample provides information regarding the relative position of the first double-stranded DNA sample within a principal double-stranded DNA sample from which the first double-stranded DNA sample was derived. The term "barcode" means a set of signals (e.g., from fluorescent labels spaced apart from one another) that represent a structural characteristic of a sample (e.g., the distance between two labels may be correlated to the presence of an extra copy of a gene in the region between the labels). The "barcode" can also be used to identify a particular sample where the set of signals from labels disposed on the sample is unique to that sample or distinguishes that sample from other samples under study.

For example, a user may determine that a portion of the barcode on a first sample taken from a "parent" sample overlaps with the barcode on a second sample taken from the "parent" sample, thus indicating that the "parent" sample included the region common to the first and second samples. Such "parent" samples may be digested to give rise to smaller oligonucleotides, which can then be themselves analyzed by the various methods described herein and then, by "barcoding" the smaller oligonucleotides, the user can then determine the relative positions of the oligonucleotides in the "parent" sample.

This is shown in FIG. 13, which depicts (graphically) the steps of digesting a parent sample of DNA, placing barcodes on the products that result from the digestion, and the alignment—suitably done by computational methods—of products having corresponding barcodes so as to piece together the parent and the effective barcode for the parent. In this way, the user can then correlate the barcode on the parent to, for example, physiological conditions in a subject. This can be done where the restriction enzymes used to digest the parent are known to isolate genomic regions that may contain copy number variations, exons, or other mutations that can be detected by comparing the distance between two labels disposed on the region of interest to the distance between two labels that are disposed on a "control" or "standard" that is known to lack (or to possess) the mutation or exon of interest.

As a non-limiting example, the user may place—by methods described here—a barcode of labels on the digestion products of a "parent sample" and then computationally reassemble those products to reform the "parent," with barcode. The user can then compare the barcode of the "parent" to other known samples to determine one or more characteristics of the parent, such as copy number variations, addition or deletion of exons, and the like. In this way, the user can perform a qualitative assessment of a "parent" sample by, effectively, placing all of the digestion products and their barcodes in their proper context within the "parent."

The methods can suitably include nicking a second double-stranded DNA sample with a sequence-specific nicking endonuclease, incorporating one or more dye-labeled nucleotides at two or more nicking sites effected by the nicking endonuclease, linearizing a portion of the second double-stranded DNA sample that includes at least two dye-labeled nucleotides, and registering (e.g., recording or noting) the relative positions of two or more labeled dye-labeled nucleotides.

These relative positions—i.e., the barcode—of the labels can (as previously described) be used to determine the relationship between the first and second double-stranded DNA samples in a primary double-stranded DNA sample from which the first and second double-stranded DNA samples were derived.

Figure 10:
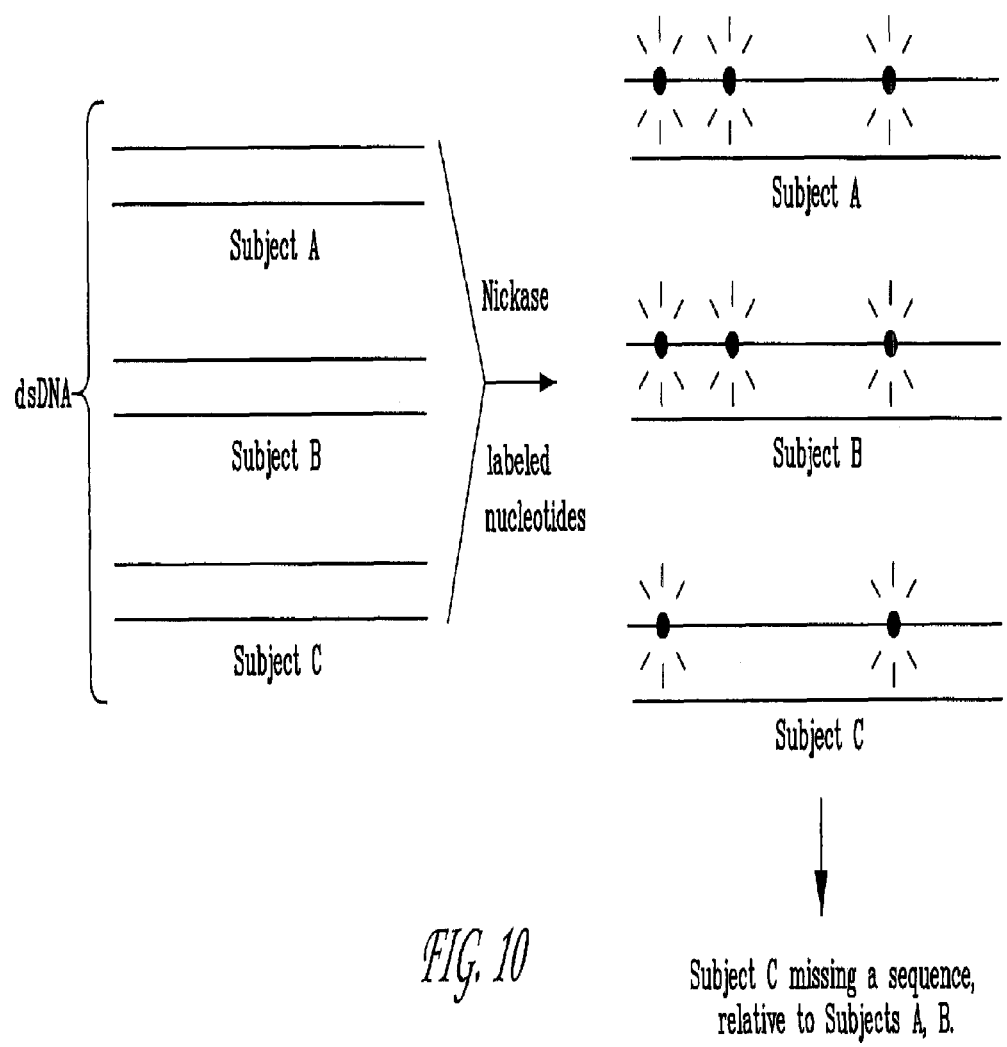
Figure 11:
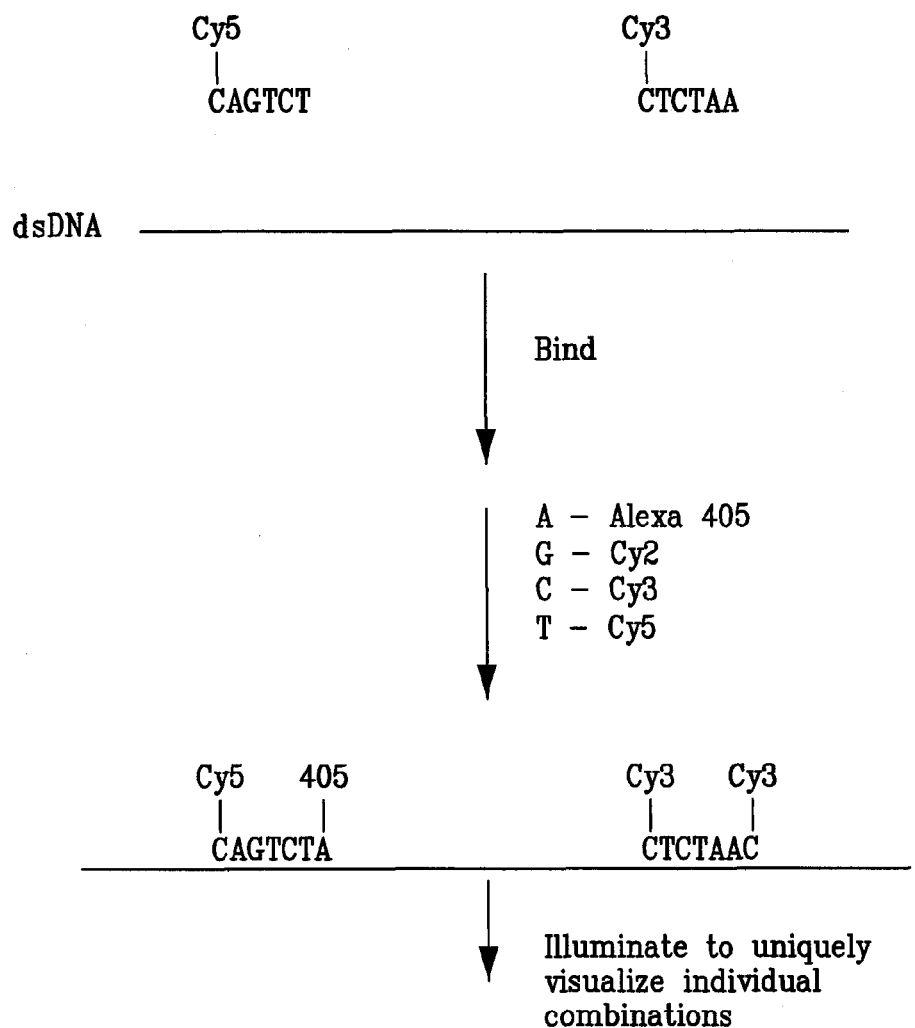

In some embodiments, the user compares the relative positions of the two or more dye-labeled nucleotides to the positions of the same dye-labeled nucleotides on a second double-stranded DNA sample contacted with the same nicking endonucleoase. In this way, the user can compare the "barcodes" on different samples taken from different sources. This enables a qualitative comparison between multiple samples, as shown in FIG. 10. In that figure, samples from Subjects A, B, and C and processed according to the claimed methods. As shown, Subject C's sample lacks a label that bound to the samples from Subjects A and B, suggesting that Subject C's DNA lacks that particular region. The user may then correlate this deleted region to a physiological characteristic of Subject C, or may compare Subject C's results to the results of still other subjects to identify those characteristics common to individuals missing that region of DNA.

Also provided are methods of obtaining sequence information about a nucleic acid biopolymer. These methods suitably include binding a first fluorescently labeled sequence specific probe having a first binding sequence to a single-stranded nucleic acid biopolymer. This is shown in, e.g., FIG, 11. The user then contacts the single-stranded nucleic acid biopolymer with a first terminator nucleotide bearing a fluorescent label A (e.g., adenine bearing Cy5), with a second terminator nucleotide bearing a fluorescent label B (e.g., cytosine bearing Alexa 405), with a third terminator nucleotide bearing a fluorescent label C, and with a fourth terminator nucleotide bearing a fluorescent label D. The user then illuminates the nucleic acid biopolymer so as to determine the presence (or relative positions) of the first terminator nucleotide, the second terminator nucleotide, the third terminator nucleotide, the fourth terminator nucleotide, or any combination thereof, adjacent to the first labeled sequence-specific probe.

The binding sequence of the first probe is suitably between 4 and 6 nucleotides. In some embodiments, the fluorescent labels of the nucleotides have different excitation wavelengths. In others, two or more of the labels share an excitation wavelength. The excitation nwavenength of a labeled nucleotide may be the same—or different—from the excitation wavelength of the labeled, sequence-specific probe.

The methods also suitably include contacting at least four fluorescently labeled probes having, respectively, second, third, fourth, and fifth binding sequences to the single-stranded nucleic acid biopolymer. The second binding sequence is suitably constructed by eliminating the base at the 5' end of the first binding sequence and adding a first replacement base to the 3' end of the first binding sequence.

Similarly, the third binding sequence is constructed by eliminating the base at the 5' end of the first binding sequence and adding a second replacement base to the 3' end of the first binding sequence. The fourth binding sequence is suitably constructed by eliminating the base at the 5' end of the first binding sequence and adding a third replacement base to the 3' end of the first binding sequence, and the fifth binding sequence is constructed by eliminating the base at the 5' end of the first binding sequence and adding a fourth replacement base to the 3' end of the first binding sequence. These probes suitably bear different fluorophores from one another, and may bear different fluorophores than the first probe.

As a non-limiting example, the first probe may comprise the sequence 5'-CTAGC-3'. In the second cycle of probing, the C at the 5' end of the probe is eliminated, and the T then becomes the 5' end of the probe, with the 3' end of the probe being as follows: 5'TAGCA-3'; 5'-TAGCT-3'; 5'-TAGCG-3'; 5'-TAGCC-3'. These labeled probes are then contacted to the biopolymer, and by illuminating the probes with the appropriate excitation wavelength, the user may determine the location of the new probes and thus obtains information regarding the sequence of the biopolymer under study. While the binding sequence shown in this example is 5 bp in length, binding sequences are suitably from 1 to 100 bp in length, but more suitably from 4 bp to 6 bp in length.

The methods also suitably include illuminating the nucleic acid biopolymer so as to determine the presence (or relative positions) of the first terminator nucleotide, the second terminator nucleotide, the third terminator nucleotide, the fourth terminator nucleotide, or any combination thereof, adjacent to the second labeled sequence-specific probe.

FIG, 11 is one non-limiting embodiment of the methods. As shown in that figure, the user may bind first and second probes—having different binding sequences—to the biopolymer sample. The user then contacts the sample with labeled nucleotides under such conditions that only a single nucleotide binds to the single-stranded DNA, adjacent to the bound probe. This gives rise to a given probe-nucleotide pair displaying two labels, which labels may—as shown in the figure—be different from one another. The user can then illuminate the sample as needed to visualize or otherwise locate the probe-nucleotide pairs. Probes and nucleotides may be joined by ligases. In some embodiments, there may be a gap (1+bps) between the probe and the nucleotide, which gap can be filled by a polymerase and a supply of nucleotides, which nucleotides may themselves be labeled. Ligase may also be used to join to probes, with the gap being 'filled in' by labeled nucleotides. Non-fluorescent probes may be used.

The user may, after completing a first cycle of probe-binding followed by binding of labeled nucleotides, begin a second cycle using probes that consider the sequence information learned in the first cycle. For example, a first probe may have a sequence of AAGG, and the labeled nucleotide that binds adjacent to the probe is T. In the next cycle, the user may take advantage of this information and use a probe that has a sequence of AGGT, so as to obtain additional sequence information, as described above.

In another aspect, the present invention provides methods of obtaining structural information about a nucleic acid biopolymer. These methods suitably include (a) contacting a double-stranded biopolymer with a nicking endonuclease so as to give rise to at least two nicking sites; (b) contacting the at least two nicking sites with a first nucleotide bearing a fluorescent label A (e.g., Cy3); (c) removing excess first nucleotide; (d) illuminating the double-stranded biopolymer so as to determine the presence or relative positions of the first nucleotide; (e) contacting the at least two nicking sites with a second nucleotide bearing a fluorescent label B (e.g., Cy5) and (f) removing excess second nucleotide. The user suitably illuminates double-stranded biopolymer so as to determine the presence or relative positions of the second nucleotide.

The user suitably contacts at least two nicking sites with a third nucleotide bearing a fluorescent label C (e.g., Alexa 405); removes excess third nucleotide; (j) illuminates the double-stranded biopolymer so as to determine the presence or relative positions of the third nucleotide. The methods also include (k) contacting the at least two nicking sites with a fourth nucleotide bearing a fluorescent label D, (l) removing excess fourth nucleotide; and (m) illuminating the double-stranded biopolymer so as to determine the presence or relative positions of the first nucleotide.

In this way, the nickase "opens" the double-stranded sample so as to make available a nucleotide adjacent to the location where the nickase binds. The user then introduces the first labeled nucleotide (e.g., cytosine), and assays the biopolymer to determine whether and where that nucleotide may have bound. This is then repeated with the other nucleotides (guanine, tyrosine, adenosine), following the introduction of each of which the user assays (via illumination) for binding of each newly-introduced nucleotide.

The preceding steps (identified as (b) through (m)) may then be repeated so as to enable the user to obtain additional sequence information with the addition of each successive labeled nucleotide.

The illumination also suitably establishes the relative positions of one or more of the labeled nucleotides. At least a portion of the sample bearing two or more labels is suitably linearized for this analysis. The user then determines the distances between the two or more labeled nucleotides residing within the linearized portion of the double-stranded biopolymer. These distances may then be used to arrive at a barcode for the sample under analysis.

In some variations, the user may induce a second nicking site adjacent to the terminator nucleotide residing at the first nicking site. The user suitably contacts the second nicking site with a first nucleotide bearing a fluorescent label A, with a second nucleotide bearing a fluorescent label B, with a third nucleotide bearing a fluorescent label C, and with a fourth nucleotide bearing a fluorescent label D, and illuminating the doublestranded biopolymer so as to determine the labeled nucleotide incorporated at the second nicking site.

Figure 12:
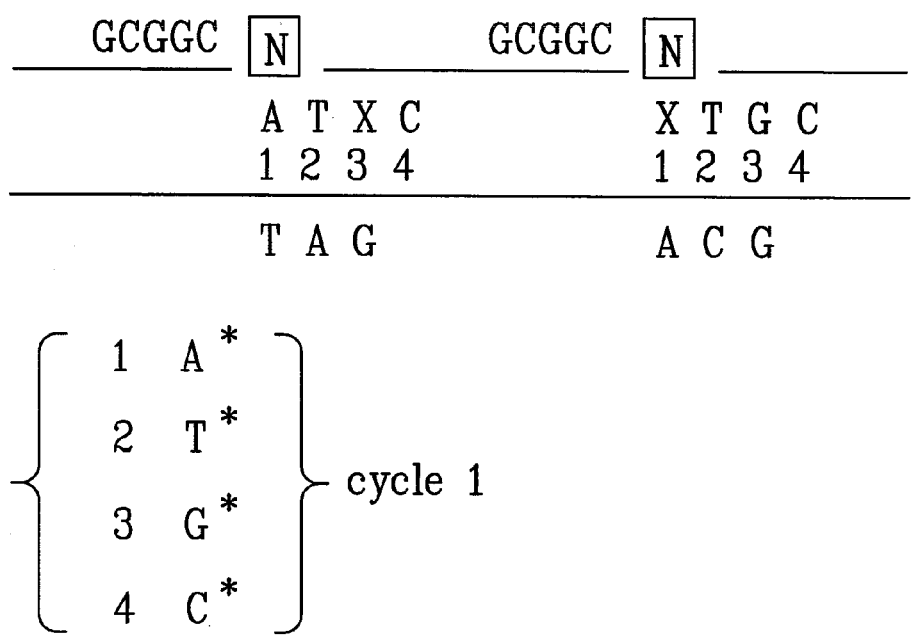

This is shown in FIG. 12. As shown in that figure, two nickase molecules bind to a double-stranded DNA sample and effect a nicking site at their ends, shown by the boxed "N" in the figure. The user then introduces labeled nucleotides in sequence. As shown in the figure, adenosine is introduced first and binds to the T located on the DNA strand opposite the left-hand probe. Because there is an adenosine opposite to the right hand probe, the labeled adnensine does not bind at that site, and an "X" signifies that there was no binding upon introduction of the first labeled base. Additional nickases and labeled bases are introduced, and the user is able to sequence the biopolymer target by sequential addition of labeled bases following by illumination of the labeled sample. The sequence information gleaned from the method can then be used to design probes that bind to particular sequences, which probes can then be used to "barcode" a given sample for further characterization, such as comparing the relative distances between two or more labeled probes on a first sample to the distances to the corresponding labeled probes on a different—or control—sample.

The invention also provides kits for performing multiplexed hybridization. These kits suitably first include a plurality of hybridization probes. Each of the probes is suitably of a different color or responds to a different excitation wavelength. The kits also suitably includes instructions for applying at least two of these hybridization probes to a nucleic acid sample, for linearizing the labeled sample, and for imaging at least one of the hybridized nucleic acids. In some embodiments, the user images two or more hybridized probes so as to determine the distance between the two probes or the relative positions of the two probes.

Depending on certain conditions, the user may populate the enture biopolymer region between adjacent nicking sites with labeled nucleotides. This is suitably accomplished when the nicking sites are comparatively close to one another. Under illumination, biopolymer regions that bear at least some labeled nucleotides are comparatively bright; regions that lack labeled nucleotides are comparatively dark. The user, however, may nonetheless glean information from both bright and dark regions.

So-called bright regions provide sequence information, as the user can illuminate the region with the excitation wavelengths that correspond to the various labeled nucleotides disposed within the region. In other embodiments, the user can, by determining the distance between bright regions (or even nucleotides) that flank a dark region, assess whether the dark region—by virtue of its size—comprises copy number variations, exons, or other structural features of interest. Thus, structural information can be gleaned from both bright and dark regions.

In some embodiments, the user may elect to utilize nickases that have binding sequences complementary to a region on the biopolymer sample that is of particular interest. In this way, the user can efficiently obtain sequence information for only that region (or regions) believed to be of greatest interest or importance.

The user may also suitably determine the sequence of at least a portion of the biopolymer sample by correlating the order of fluorophores visible under illumination to the nucleotides to which one or more of the fluorophores correspond.

Additional Disclosure

Imaging Techniques

Several techniques improve optical resolution in fluorescent imaging by at least one order of magnitude. Application of these imaging techniques to single molecule DNA and RNA analyses vastly accelerates the applications discussed above.

One such technique, termed Fluorescence Imaging with One Nanometer Accuracy (FIONA), involves the localization of single organic fluorophores by fitting a distribution function to the light collected from the fluorophore. The center of this distribution can be localized with 1.5 nm precision. FIONA has been used to study the translocation of molecular motors or to measure small distances.

Extensions of this technique include Single molecule-High Resolution Imaging with Photobleaching (SHRIMP) which is able to resolve adjacent fluorophores of the same color with about 10 nm resolution. FIONA has been extended to two colors, developing a method termed single-molecule high-resolution colocalization (SHREC). Users might, for example, colocalize Cy3 and Cy5 dyes as close together as 10 nm, which dyes can be attached at the ends of a short DNA. Also useful is a method of multicolor stochastic optical reconstruction microscopy (STORM), which allows combinatorial pairing of reporters and activators. Iterative, color-specific activation of sparse subsets of these probes allows localization with nanometer accuracy.

Genome Mapping Methods

Structural variations play a very important role in human health and common diseases. These variations are defined as being longer than 11 kb. But despite their importance, most genome-wide approaches for detecting copy number variations (CNVs) are indirect, depending on signal intensity differences between samples and controls to predict regions of variation. Such approaches therefore provide limited quantitative signal and positional information, and cannot detect balanced events such as inversions and translocations. For example, microarray-based platforms including SNP array, oligo Comparative Genomic Hybridization (CGH) array, and BAC CGH arrays are the main techniques for structural variations discovery. Non-uniform sensitivity, specificity, and probe density of these platforms often lead to conflicting results even with identical samples. This qualitative measurement requires further confirmation by low throughput detection methods, such as PCR and FISH.

Optical Mapping

The single molecule techniques described above are well suited for studying structural variations. However, due to the optical nature of the mapping, they are limited in their ability to resolve motifs that are closer than about ~1 kbp. Significantly greater mapping efficiency can be achieved by resolving features less than 100 bp apart. In turn, this substantially improves our ability to identify structural variations in native, long genomic DNA molecules.

A suitable mapping scheme is based on the labeling of sites generated by nicking endonucleases. A nicking endonuclease with a five base recognition sequence will, on average, generate a 1 kb physical map across the whole genome. Based on in silico whole genome mapping, a large portion of such nicking sites fall within 1000 bp of each other, which distance which cannot be resolved with conventional optics. This reduces map resolution and makes map assembly more difficult.

An example is the recognition sequences (motifs) for two commercially available nicking endonucleases ranging with 5 base to 7 base recognition sites. An algorithm to map all the nicking sites against the human reference genome was designed.

In the case of enzyme Nt.BstNB1 (5 base motif GACTC), there are $2.1 \times 10^6$ sites across whole human genome, which produces an average of 1.5 kb between nicks. For enzyme Nt.BspQ1 (7 base motif GCTCTTC), there are $2.2 \times 10^5$ nicking sites separated on average by 15 kbp. In principle, the nicking sites using the 5 base motif are resolvable with conventional optics (~1 kbp), but in silico analysis revealed that almost half the nicking sites fall within 1kbp of each other, rendering them indistinguishable from one another. Using the 7 base motif, one can resolve a greater number of sites. As discussed below, this leads to challenges in uniquely mapping a fragment of DNA.

Improved Resolution in DNA Mapping

In silico mapping was used to determine the percentage of DNA fragments that can be uniquely mapped based on currently available nicking enzymes and our existing optical detection system.

Figure 1A:
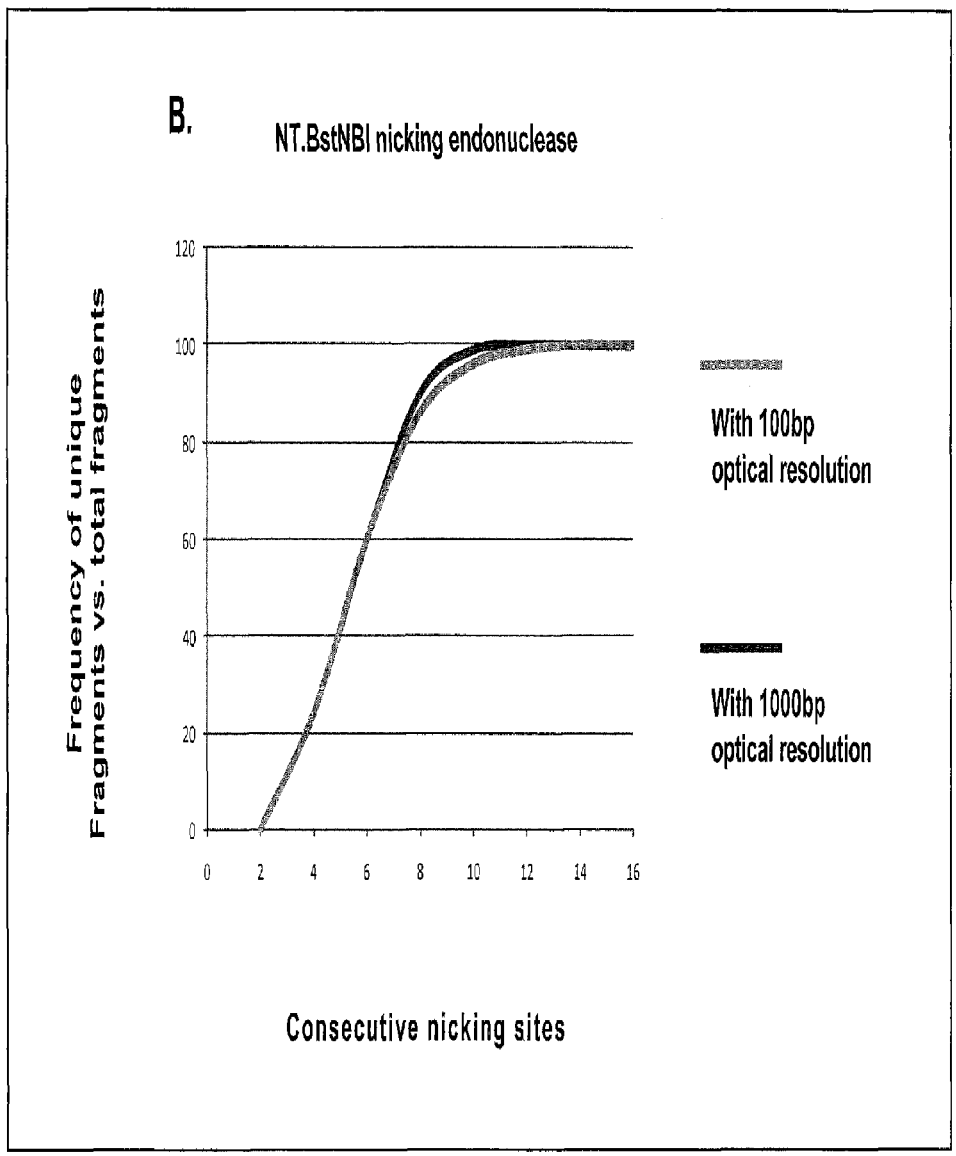
FIG. 1A illustrates mapping statistics for Nt.BstNBI nicking endonuclease demonstrating that 100 bp optical resolution dramatically improves the map accuracy and coverage.

FIG. 1A shows the results for the nicking endonuclease Nt.BstNBI (5 base motif). For 1000 bp optical resolution, only about 12% of fragments can be uniquely identified with 8 nicking sites. On the other hand, to achieve 100 by resolution, over 97% of the fragments are unique. Closely clustered nicking sites pack more sequence information and their distributions are unique. Furthermore, with only 8 nicking sites, one merely needs a 12 kb fragment (on average) to enable unique mapping of the fragment to the reference genome.

Figure 1B:
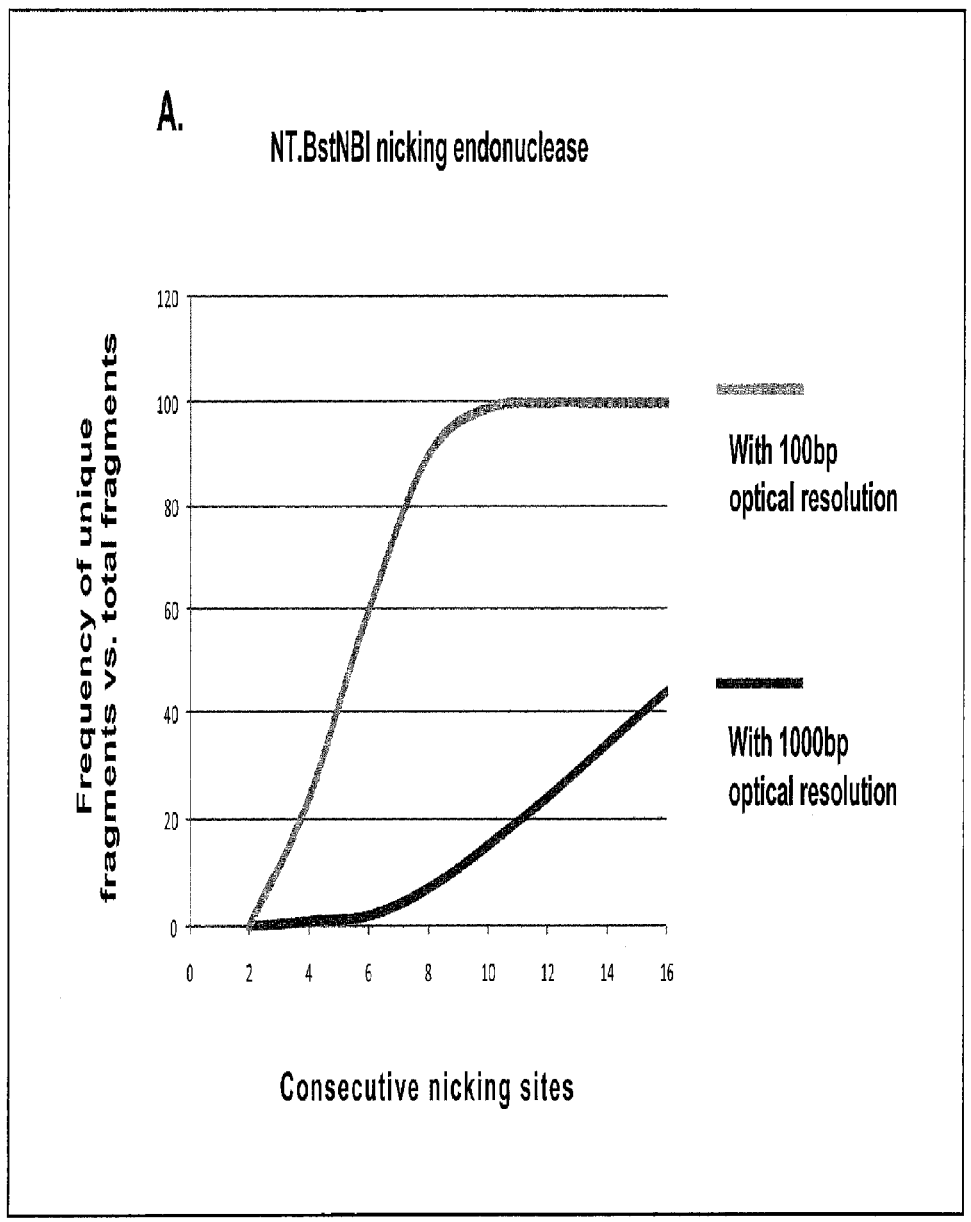
FIG. 1B illustrates unique mapping statistics for Nt.BspQI nicking endonuclease, demonstrating that 100 bp optical resolution has little impact on the map accuracy and coverage.

The nicking map for enzyme Nt.BspQI (7 base motif) (FIG. 1B) shows that by improving the resolution to 100 bp, one gains very little because fewer Nt.BspQI nicking sites fall within 1kbp of each other. On average 8 consecutive Nt.BstQI nicking sites are needed to uniquely identify a DNA fragment using this enzyme but the average size of fragments is about 120 kb. There are significant regions of the genome (~30%) that cannot be mapped due to the lack of consecutive nicking sites within a length of DNA that can be reasonably extracted with existing methods.

Without being bound to any single theory, some advantages of the claimed invention can be identified. First, much more information about a DNA fragment is available when resolving closely spaced nicking sites. The ability to uniquely map a fragment to the genome is vastly improved.

Second, with improved resolution, one may resolve much smaller structural variations than is currently possible with optical methods. Finally, improved resolution also helps us identify large scale structural variations.

Additional Background on the Figures

Figure 1C:
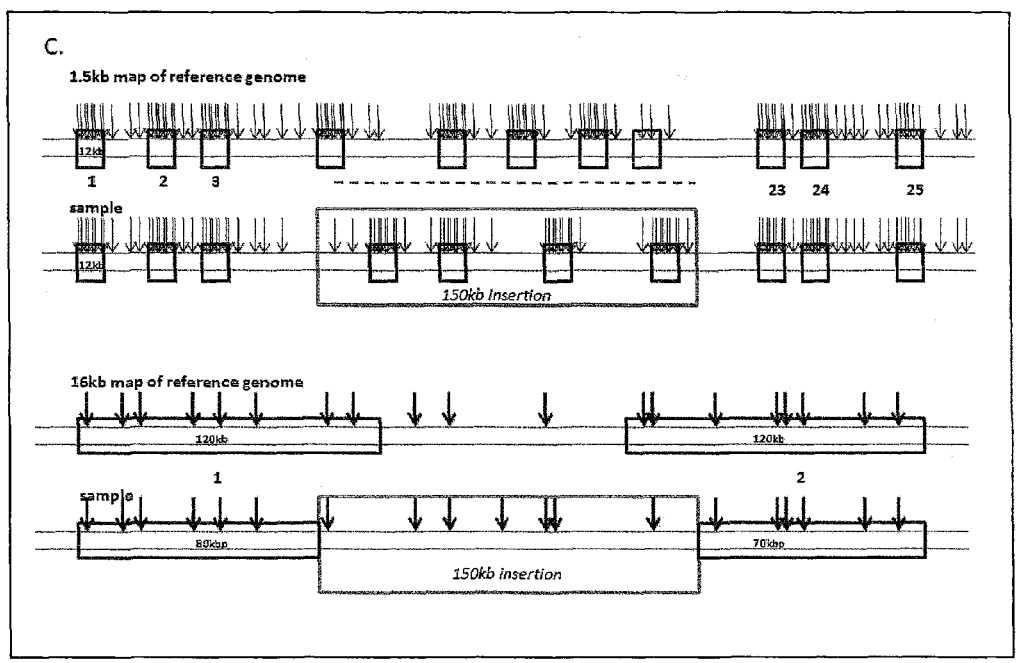
FIG. 1C illustrates that a comparatively fine map (1.5 kb) has better detection power for structural variations than does a comparatively coarse map (16 kb)
Figure 2A:
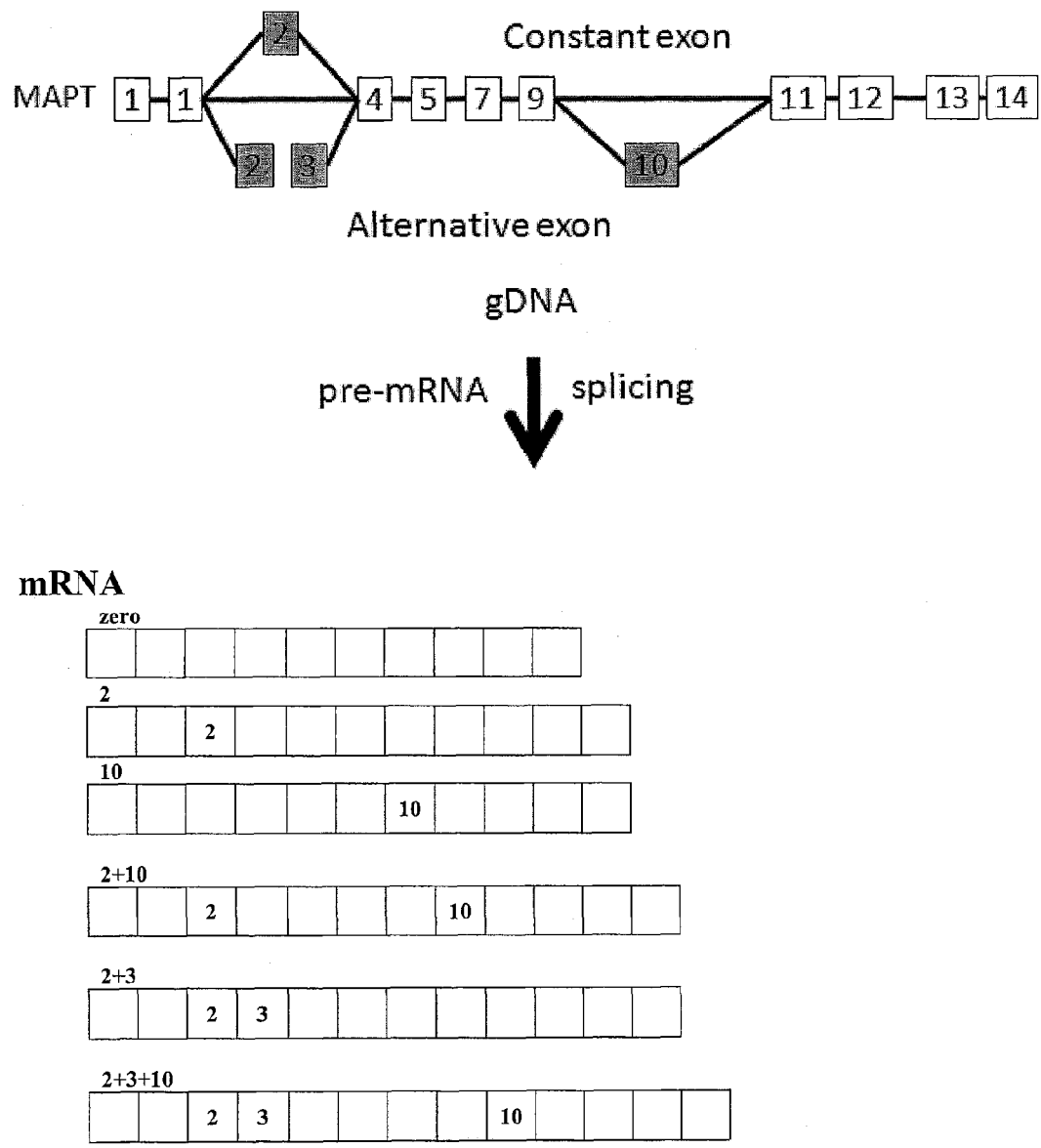
FIG. 2A depicts MAPT gene structure.
Figure 2C:
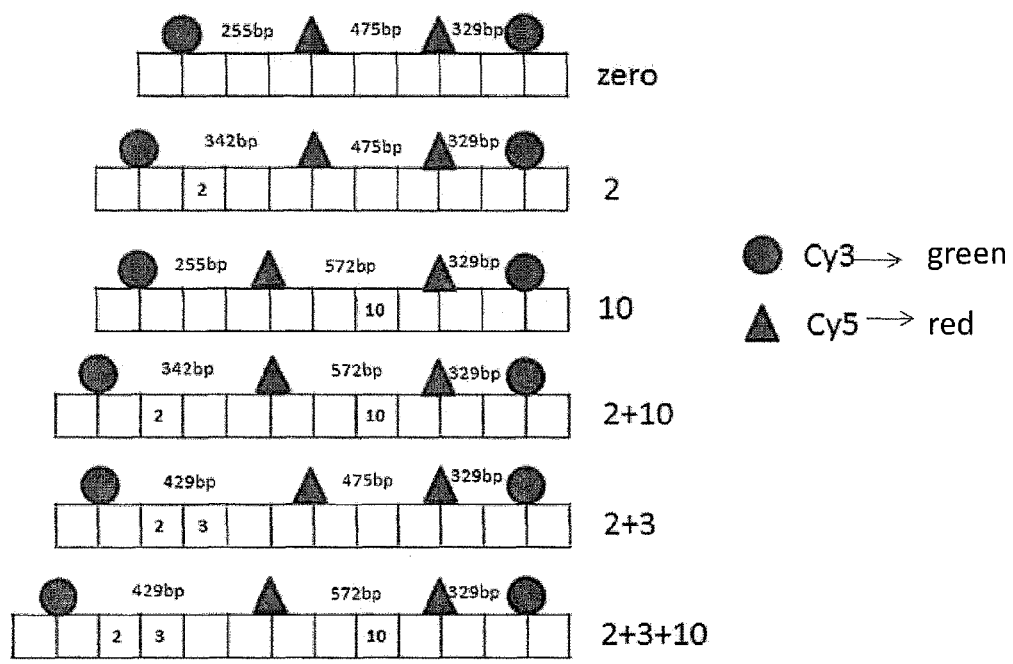
FIG. 2C illustrates a barcoding or mapping scheme for super resolution imaging as applied to RNA exon splicing.
Figure 3:
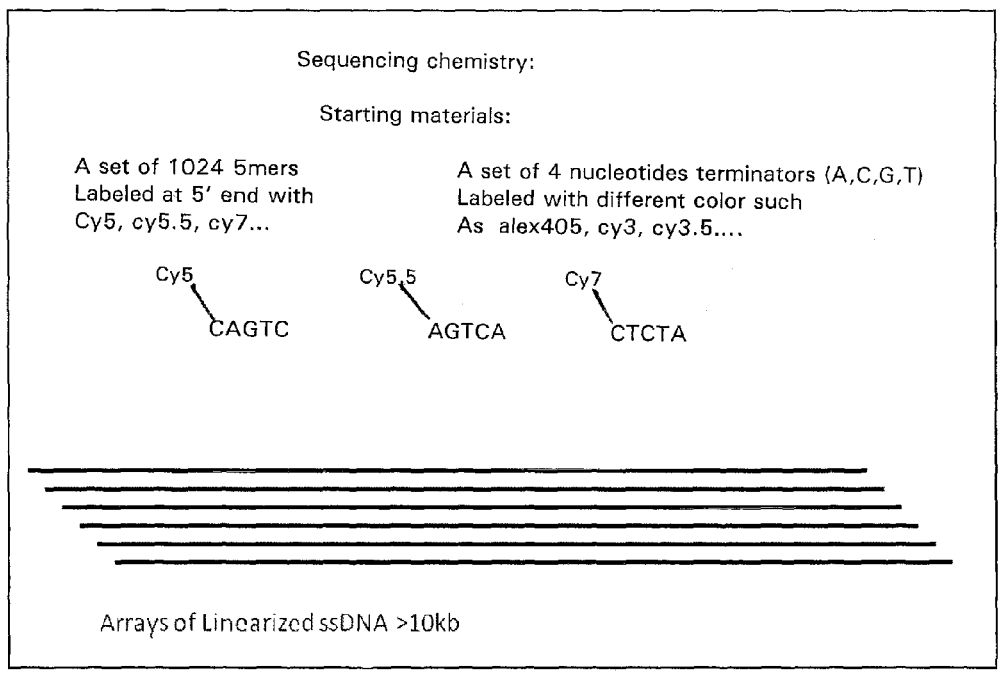
FIG. 3 illustrates starting materials for sequencing.
Figure 7A:
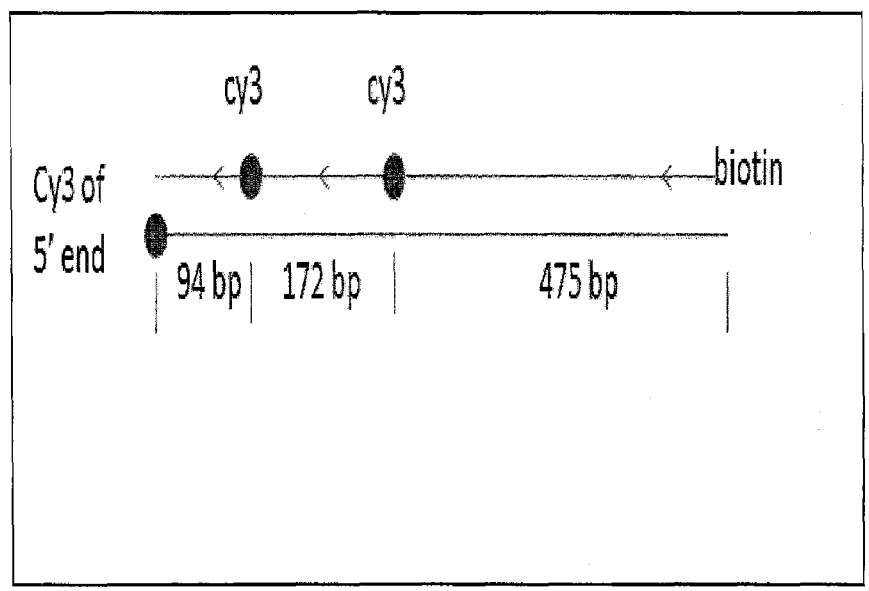
FIG. 7A depicts a model system of 741 bp PCR product used to demonstrate the resolution of SHRIMP.
Figure 7B:
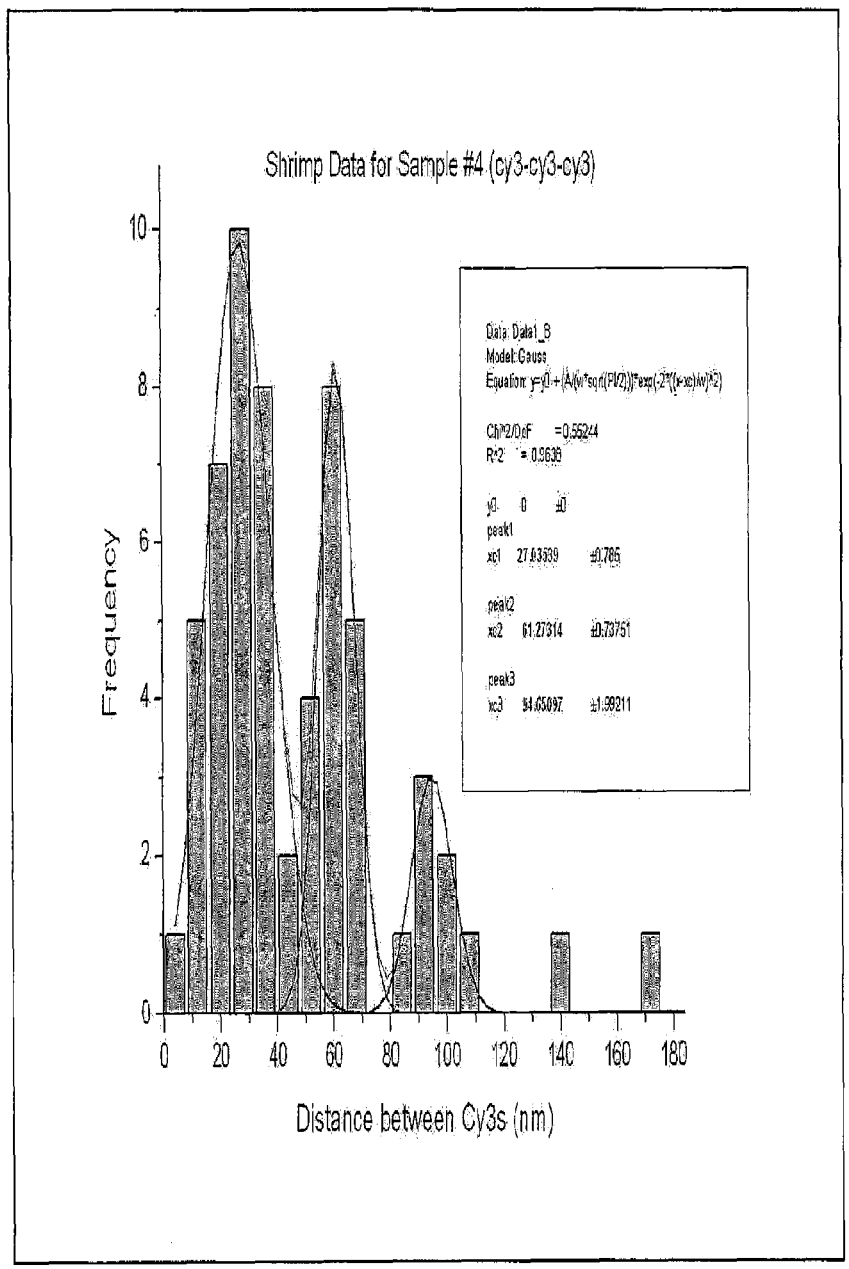
FIG. 7B illustrates imaging results after labeled DNA molecules were linearized on glass surface, indicating three (3)

In FIG. 1C is shown an example of a fragment having a 150 kbp insertion. Successfully mapping the fragment (and thus identifying the location of the insertion within the genome), can use a contiguous set of 8 nicking sites adjacent to the insertion. With limited optical resolution, this necessitates large (>300 kbp) genomic fragments. These are difficult to generate with standard DNA extraction protocols. In contrast, with 100 bp resolution, one may employ a dense nicking site distribution using a fragment only slightly larger than the insertion to uniquely map the fragment.

The Need for High Throughput Digital Profiling of Alternative Transcriptome

Another nucleic acid analysis that can greatly benefit from improved mapping capability is alternative splicing of RNA. During pre-RNA splicing, introns are removed, and exons are joined together to form mature RNA. Alternative splicing is the process by which a single primary transcript yields different mature RNAs. This leads to the production of protein isoforms with diverse and even antagonistic functions. Recent studies showed the large proteomic complexity and diversity are achieved with a limited number of genes. In human genome, ~75% of human genes exhibit alternative splicing. While the human genome contains 25,000 genes, it can produce several hundred thousand different types of proteins through alternative splicing.

Alternative splicing variants of many genes have a critical impact on all major aspects of cell biology, including cell cycle control, apoptosis and more. Aberrant splicing has been found to be associated with various diseases, including cancer, and recent studies suggest that mRNAs are more frequently alternatively spliced in cancerous tissues than in normal ones. Other examples include the significant reduction of the full-length transmembrane conductance regulator (CFTR) gene due to aberrant exon inclusion and inclusion which gives rise to atypical forms of Cystic Fibrosis. Another example is the microtubule associated protein Tau (MAPT gene). MAPT is required for the polymerization and stability of microtubules as well as axonal transport in neurons. Aberrant splicing of Tau exon 10 leads to the development of neurodegenerative disease, dementia FTDP-17.

A number of techniques have been developed to quantify RNA splicing variants. First, oligo microarray and fiber-optic arrays have been used for globally detecting gene splicing variants. However, because small fragments of full RNA transcripts are interrogated one at a time in array technology, only one splicing event (two exons at a time) can be detected at a time. Thus, it is difficult to quantify how many exons are included or excluded in one specific splicing variant. Furthermore, non-specific hybridization can result in many false positives which require further confirmation.

Second, real-time PCR can obtain splicing information by quantifying one exon junction at a time but is limited by stringent reaction conditions, low throughput, and high cost. Third, so-called next generation sequencing technologies have been employed in digital gene expression profiling and could be used in profiling alternative splicing variants. However, they are largely based on short sequence reads and have the same limitations as microarrays with regards to full-length RNA samples.

A disadvantage common to existing transcriptome-focused technologies is that none is capable of monitoring combinations of alternatively spliced exons, as they occur within individual transcripts. Under existing methods, exon exclusion is hard to confirm, which may result in false exclusion of certain exons.

Despite the enormous importance of alternative splicing to mammalian biology, current solutions to deciphering this problem face challenges. Indeed, little is known about how alternative splicing is regulated and coordinated through the developmental stage due to a lack of robust methods to quantify RNA splice variants.

Improving Resolution Beyond Conventional Optical Limitations

As an example of the advantages available to improved resolution, one can consider an optical barcoding approach for microtubule associated protein Tau (MAPT) gene which is required for the polymerization and stability of microtubules as well as axonal transport in neurons. Aberrant splicing of Tau exon 10 leads to the development of neurodegenerative disease such as dementia FTDP-17.

An exemplary RNA barcoding scheme is shown in FIG, 2. Three exons (2, 3, and 10) in MAPT transcripts can undergo alternative splicing, exon 2 and exon 3 are always spliced together. Thus, six different MAPT transcripts can be generated by alternative splicing. The MAPT gene structure is shown in FIG, 2A.

All six possible alternative splicing isoforms are indicated (Zero, 2, 10 2+10, etc.), and the length of each exon is indicated in FIG, 2B. Conventional optical resolution unable to discriminate labels associated with different exons. If the position of the exons could be resolved, the measured distance between the labels will identify each splicing variant in a manner similar to reading a barcode.

To form a barcode in this example, four exon specific oligo probes could be designed to specifically hybridize to exon 1 (Cy3-green), exon 7(Cy5-red), exon 11(Cy5-red), exon 13 (Cy3-green) respectively, as shown with green and red arrows in FIG, 2C. The distance between the labels can be used to identify which variant is present and the color sequence (i.e. Green-Red-Red-Green) indicates the presence of a fully labeled transcript. Further, the disclosed barcoding scheme is easily multiplexed.

For example, if the same two colors (e.g., green and red) with four different probes were used to tag a different gene, a color sequence can be designed for this particular gene that is different from that of the MAPT gene. The sequence of color can thus be used to define the specific gene and the distance between the labels of that color sequence determine the individual splicing variant of that specific gene. In this two-color, four-probe approach, there are $2^4=16$ different color sequences to interrogate 16 different genes simultaneously with unlimited power for splicing variants. If 4 colors of 8 different probes were used, $4^6=65536$ different genes can be investigated simultaneously, which is more than the entire human transcriptome (FIG, 2C).

This approach has three important advantages over current expression profiling technologies for interrogating RNA splicing: (i) By mapping the distribution of exons within a single transcript concurrently, one can determine the relationships amongst multiple alternatively spliced exons within the same transcript. (ii) The digital nature of the barcoding scheme means not only can one quantify the individual splicing variant, one can quantify the total gene expression by adding up the all the splicing variants. (iii) The barcoding scheme will provide maximum multiplex detection capability. Realizing these advantanges necessitates an imaging technology with resolution that far exceeds conventional optical approaches.

The Need for Low Cost and High Throughput Whole Genome Sequencing

The success of the Human Genome Project (HGP) is largely due to the continuous development of Sanger sequencing method through parallelization, automation, miniaturization, better chemistry and informatics. As the workhorse of the Human Genorne Project, Sanger sequencing method has dominated the DNA sequencing field for nearly three decades, and its 800 Q20 base read length is significant.

These newly emerging sequencing technologies can be grouped into two categories based on the detection methods, sequencing either by ensemble detection or by single molecule detection. Since multiple DNA copies are needed in ensemble detection, the genetic information, such as haplotype and RNA splicing pattern is lost during the process. While sequencing by single molecule detection may be able to recover haplotype information, the read length of current single molecule sequencing method (e.g., Helicos tSMS) is 50 bp or less, which is far shorter than the average distance of 1 kbp between two SNPs. Thus, as with the predecessor Sanger sequencing method, critical genetic information such as haplotypes and RNA splicing pattern is still difficult to obtain with these "next generation" sequencing technologies. The present invention, among other things, effects DNA sequencing length over 10 kb.

Sequencing by hybridization is a well known method that employs microarray-based hybridization assays to determine the sequence of nucleic acid molecules. Normally, short oligos with known sequence (<100mer) constructed on a microarray are used to capture (i.e., hybridize) and interrogate the target molecules. The microarray assays produce a list of all subsequences of hybridized oligos found at least once in the target molecules. However, the list does not reveal the locations of the sequences of hybridized oligos or nor does the list provide the number of the times an oligo may be present on a target molecule. The present invention, however, obtains such information.

FIG, 3 displays the starting materials for sequencing. A set of 5-mer (i.e., five nucleotides in length) oligos with 5' end labeled with different color fluorophores; 4 nucleotide terminators labeled with different color fluorophores; arrays of linearized single stranded DNA molecules, or double stranded DNA molecules with partial ssDNA gaps.

FIG, 4 describes the first cycle of an exemplary sequencing reaction. After the first cycle, each hybridization and incorporation events are recorded and localized alone linearized DNA molecules by STORM imaging technique. The probes are then washed away. In the next cycle, 4 more 5-mer probes AGTCA, AGTCT, AGTCG, and AGTCT are introduced and hybridize on the same locations as previous probes, as they share the same sequences as previous probes. A polymerase then incorporates the nucleotide terminators (FIG, 5).

This process is adapted to be multiplexed (using labels of different colors) and to produce large number of sequences read during one cycle (FIG, 6). Also developed are algorithms to prioritize the sequential addition of 5-mer probes. The super imaging techniques used here included SHRIMP, SHREC, STORM.

EXAMPLES

Single-molecule high resolution co-localization (SHREC) and single-molecule high-resolution imaging with photobleaching (SHRImP) methods have been developed to measure distances between two fluorophores that are closer than Rayleigh limit (≈250 nm for visible excitation).

Combining the two techniques adds another dimension to the power of localization methodology and tens of distances could potentially be resolved by using several fluorophores of different colors each having multiple members. To apply this to DNA, double-stranded DNA was stretched on a Polyacrylic acid and Polyallylamine coated surface, making the DNA relatively straight. To test SHRIMP, a DNA construct was made with a biotin followed by three Cy-3's at positions 475 bp, 172 bp, and 94 bp, corresponding to distances between Cy3 of 32 nm, 58 nm, and 90 nm (FIG, 7B).

Additional detail is provided in FIG, 7A. One PCR primer was labeled at 5' end with cy3 and the other primer was phosphorelated at 5' end. After PCR reaction, the 5' end of cy3 protect that strand from digestion by lambda exonuclease, which resulting in a single stranded DNA molecules. Once the single-stranded DNA molecules were generated, primer extension reactions were performed to introduce fluorescent dyes at each specific sequence positions. In this case, two short oligos with cy3 at their 5' end were hybridized respectively at 94 bp and 256 bp from one end. Another short oligo with a biotin at its 5' end was hybridized at the 3' end of the single stranded template. After extension by polymerase, the single stranded template was converted to double stranded DNA molecules and two cy3 dye molecules were introduced at specific locations.

Figure 8A:
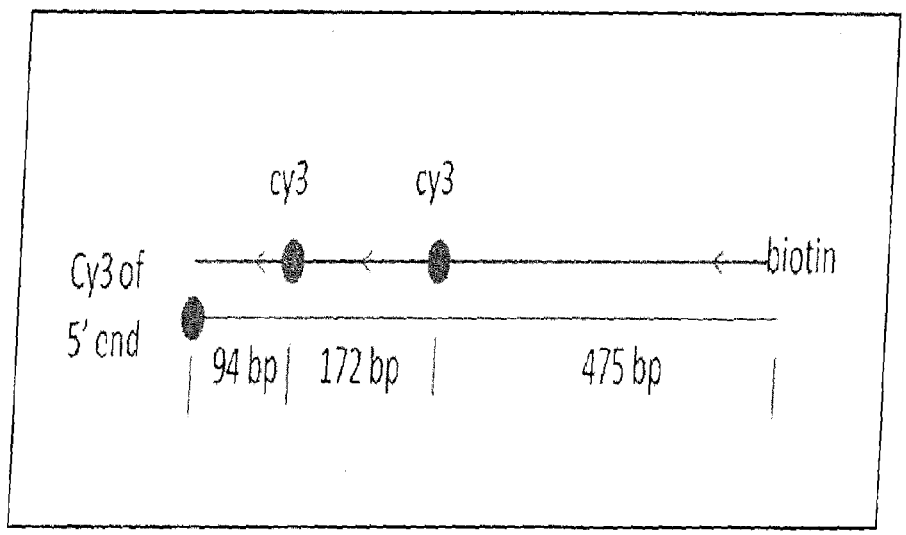
Figure 8B:
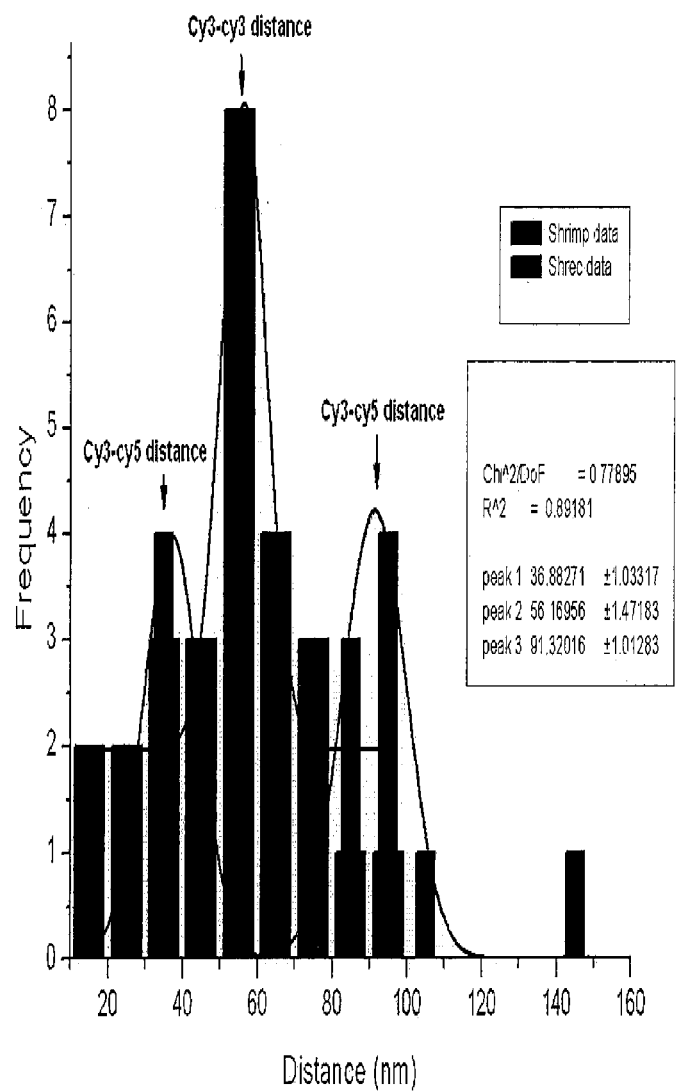

Distances of 27 nm, 61 nm, and 95 nm were measured, in excellent agreement with the expected distances. To test simultaneously SHRIMP and SHREC, Cy5 was placed at position zero, and two Cy3's at position 94 bp and position 172 bp, with their positions measured using a dual-view imaging system. The distances between Cy3-Cy5 pairs were 37±5 nm (32 nm expected) and 91±5 nm (87 nm expected), and the distance between Cy3-Cy3 pair to be 56±3 nm (58 nm expected) (FIG. 8). The agreement was excellent.

What is claimed:

1. A method of obtaining sequence information about a DNA sample, comprising:
   nicking a first double-stranded DNA sample with a first sequence-specific nicking endonuclease;
   incorporating labeled nucleotides into the first double-stranded DNA sample at two or more nicking sites effected by the nicking endonuclease;
   linearizing a portion of the first double-stranded DNA sample that includes at least two labeled nucleotides by passing the portion of the first double-stranded DNA sample through a nanochannel; and
   registering the relative positions of two or more labeled nucleotides of the portion of the first double-stranded DNA sample, wherein the portion of the first double-stranded DNA sample is residing within the nanochannel, and wherein at least two of the labeled nucleotides are separated from each other by 30 base pairs to 1000 base pairs.

2. The method of claim 1, wherein at least one of the two or more of the labeled nucleotides comprises a terminator nucleotide.

3. The method of claim 1, further comprising determining the relative position of the first double-stranded DNA sample within a principal double-stranded DNA sample from which the first double-stranded DNA sample was derived.

4. The method of claim 3, wherein the first double-stranded DNA sample was obtained from the principal double-stranded DNA sample by digestion.

5. The method of claim 1, further comprising nicking a second double-stranded DNA sample with a sequence-specific nicking endonuclease, incorporating one or more labeled nucleotides into the second double-stranded DNA sample at two or more nicking sites effected by the nicking endonuclease, linearizing a portion of the second double-stranded DNA sample that includes at least two labeled nucleotides, and registering the relative positions of two or more labeled nucleotides of the portion of the second double-stranded DNA sample.

6. The method of claim 1, further comprising comparing the relative positions of the two or more labeled nucleotides to the positions of the same labeled nucleotides on a second double-stranded DNA sample contacted with the same nicking endonuclease.

7. The method of claim 1, wherein registering the relative positions of the two or more labeled nucleotides comprises determining the distances between the two or more labeled nucleotides residing within the linearized portion of the first double-stranded DNA.

8. The method of claim 1, wherein incorporating labeled nucleotides at the nicking sites comprises contacting the nicking sites with three or more fluorescent-label-bearing nucleotides selected from a first nucleotide bearing a fluorescent label A, a second nucleotide bearing a fluorescent label B, a third nucleotide bearing a fluorescent label C, and a fourth nucleotide bearing a fluorescent label D.

9. The method of claim 8, further comprising illuminating the first double-stranded DNA sample so as to determine the presence or relative positions of the one or more fluorescent-label-bearing nucleotides.

10. The method of claim 9, further comprising determining the sequence of at least a portion of the first double-stranded DNA sample by correlating the order of fluorophores visible under illumination to the nucleotides to which one or more of the fluorophores correspond.

11. The method of claim 1, further comprising nicking the first double-stranded DNA sample with a second sequence-specific nicking endonuclease to introduce nick sites adjacent to the nucleotide residing at the two or more nick sites effected by the first sequence-specific nicking endonuclease.

12. The method of claim 1, further comprising obtaining sequence information of the DNA sample based on the registered relative positions of the labeled nucleotides.

13. The method of claim 1, wherein incorporating labeled nucleotides comprises contacting the nicking sites with two or more labeled nucleotides selected from the group consisting of a first nucleotide bearing a label A, a second nucleotide bearing a label B, a third nucleotide bearing a label C, and a fourth nucleotide bearing a label D.

14. The method of claim 13, wherein at least two of the label A, label B, label C, and label D are different.

15. The method of claim 13, wherein the nicking sites are contacted with three or more labeled nucleotides, and wherein at least three of the label A, label B, label C, and label D are different.

16. The method of claim 13, wherein the nicking sites are contacted with four or more labeled nucleotides. and wherein at least four of the label A, label B, label C, and label D are different.

17. The method of claim 1, wherein the labeled nucleotide is a dye-labeled nucleotide.

* * * * *